(12) United States Patent
Rodriguez Pierluissi et al.

(10) Patent No.: US 11,198,678 B1
(45) Date of Patent: Dec. 14, 2021

(54) **PLAKORTINIC ACIDS A AND B: CYTOTOXIC CYCLOPEROXIDES WITH A UNIQUE BICYCLO[4.2.0]OCTENE UNIT FROM SPONGES OF THE GENERA *PLAKORTIS* AND *XESTOSPONGIA***

(71) Applicants: Abimael D. Rodriguez Pierluissi, San Juan, PR (US); Carlos Jimenez Romero, San Juan, PR (US)

(72) Inventors: Abimael D. Rodriguez Pierluissi, San Juan, PR (US); Carlos Jimenez Romero, San Juan, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 15/615,788

(22) Filed: Jun. 6, 2017

Related U.S. Application Data

(60) Provisional application No. 62/346,117, filed on Jun. 6, 2016.

(51) Int. Cl.
*C07D 317/04* (2006.01)
*C07D 493/08* (2006.01)

(52) U.S. Cl.
CPC ......... *C07D 317/04* (2013.01); *C07D 493/08* (2013.01)

(58) Field of Classification Search
CPC .................................................. C07D 317/04
See application file for complete search history.

(56) References Cited

PUBLICATIONS

A R. Carroll, et al., Marine natural products, Nat. Prod. Rep., 2019, 36, 122-173.
R A. Hill, et al., Hot off the press, Nat. Prod. Rep., 2006, 23, 11-14.

*Primary Examiner* — David K O'Dell
(74) *Attorney, Agent, or Firm* — Hoglund & Pamias, PSC; Roberto J. Rios

(57) ABSTRACT

Plakortinic acids A (2) and B (3), two polyketide endoperoxides having an unprecedented bicyclo[4.2.0]octene unit, were isolated as minor constituents from the sponge-sponge symbiotic association *Plakortis halichondrioides-Xestospongia deweerdtae* from Puerto Rico, along with the known epiplakinic acid F (1). The molecular structures of 2 and 3 were determined mainly on the basis of NMR spectroscopy. Due to the structural similarities, 2 and 3 are thought to be biosynthetically related to 1. Biological screening for cytotoxic activity against two human tumor cell lines revealed that these novel metabolites are very active at low to sub-micro molar concentration.

1 Claim, 24 Drawing Sheets

Elysiapyrone A[1]

Elysiapyrone B[1]

Ocellapyrone B[1]

Kingianin A[2]

Biyouyanagin A[3]
anti-HIV activity

Biyouyanagin A[4]
cytotoxic activity

Endiandric acid D[1]

Endiandric acid E[1]

SNF4435C[2]
Immunosuppressants

SNF4435D[2]
Immunosuppressants

Shimalactone B[3]
cytotoxic activity

Shimalactone B[4]
cytotoxic activity

Ocellapyrone A[5]

Citreoviripyrone A[6]
inhibitory activity on cell growth

Expansion of the 13C NMR spectrum (125 MHz) of plakinic acid A (2) in CDCl3.

PLAKORTINIC ACIDS A AND B: CYTOTOXIC CYCLOPEROXIDES WITH A UNIQUE BICYCLO[4.2.0]OCTENE UNIT FROM SPONGES OF THE GENERA *PLAKORTIS* AND *XESTOSPONGIA*

GOVERNMENT INTEREST

This invention was made with U.S. Government support under grant number: GM086271 awarded by The National Institutes of Health (NIH). The government has certain rights in this invention.

BACKGROUND OF THE INVENTION

As part of our continuing efforts to identify new bioactive compounds from Caribbean marine sponges, we re-investigated chemically the symbiotic two-sponge association *Plakortis halichondrioides-Xestospongia deweerdtae* collected in Mona Island off the west coast of Puerto Rico. Marine sponges within the genera *Plakortis* and *Plakinastrella* represent an amazing source of cyclic peroxide-containing natural products, which in addition to their interesting biological activity, display a diverse array of molecular architectures. Interestingly, many sponges of the Plakinidae family, as well as other marine animals, often contain a plethora of straight- and branched-chain 1,2-dioxolane carboxylic acids of varying length that often incorporate multiple double bonds, terminal phenyl groups and, albeit rarely, cyclooctatriene rings (FIG. 3a). This observation entails that conjugated linear polyenes are ubiquitous in many marine species.

Indeed, previous research has demonstrated that from relatively simple (E,E,E,E)-tetraene precursors, structurally diverse scaffolds such as the bicyclo[4.2.0]octadiene core can be obtained through various modes of thermal and photochemical reactions. Thus, a suitable polyene could be encouraged by enzymes to undergo selective E/Z double bond isomerizations resulting in the necessary geometry for cascade electrocyclizations to ensue (FIG. 3b). Bicyclo[4.2.0]octane-based natural products with different substitution patterns have been reported from various sources, including plants, saccoglossan mollusks, *Streptomyces*, and marine-derived fungi as shown in FIG. 2a-FIG. 2c. Although polyene precursors could give rise, among several complex skeletons, to compounds based on a bicyclo[4.2.0]octadiene framework, thus far this type of natural products have yet to be isolated from any *Plakortis* or *Plakinastrella* species.

SUMMARY OF THE INVENTION

The present invention discloses the isolation and structure elucidation of plakortinic acids A (2) and B (3), the first two members of a new chemical series having an unprecedented bicyclo[4.2.0]octene backbone.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 4:
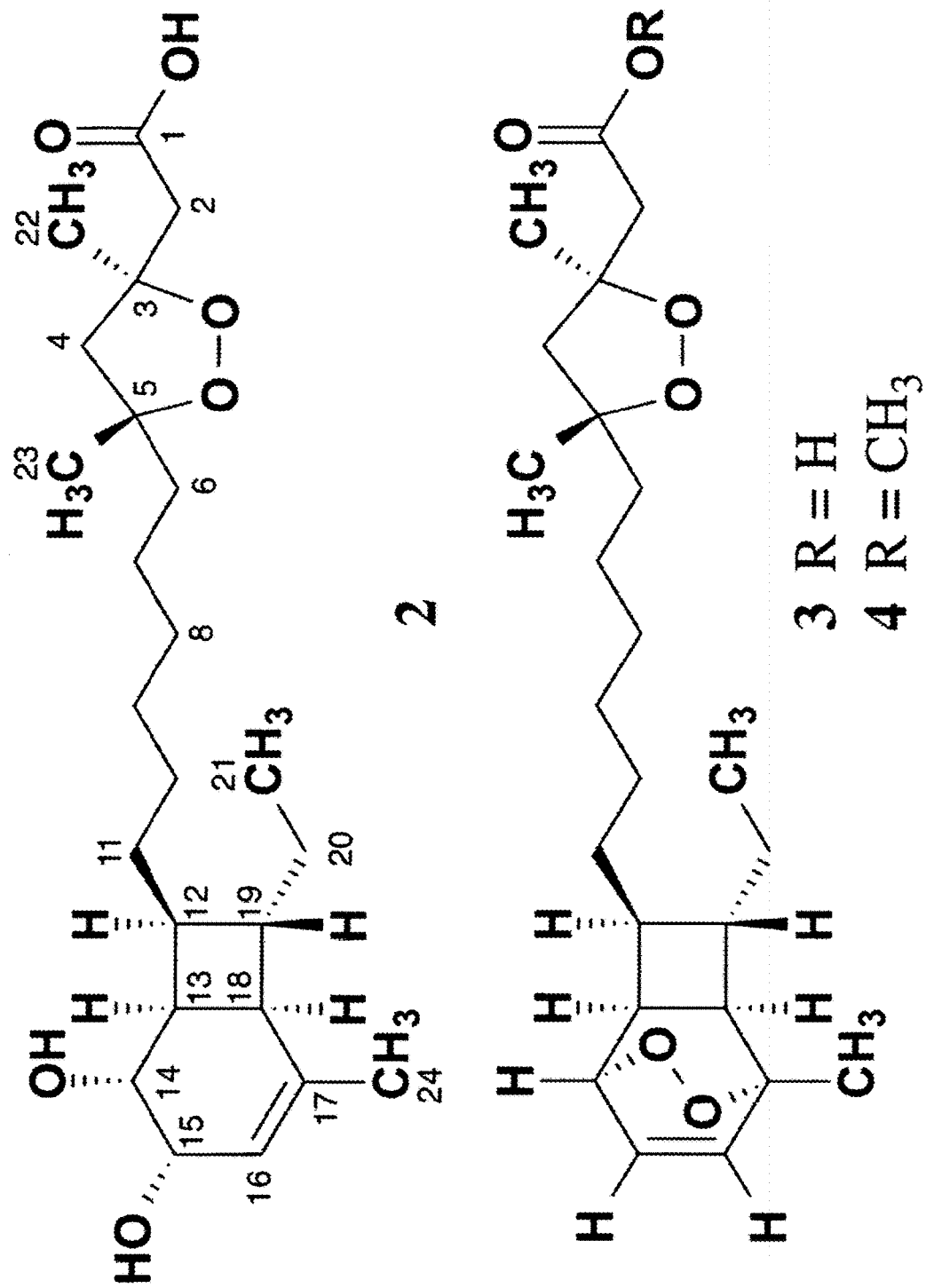
FIG. 4 shows isolated polyketide-derived metabolites plakortinic acids A (2) and B (3) having a bicyclo[4.2.0]octene backbone, according to the present invention.

In general terms, the compounds were obtained by cutting the sponge specimens into small blocks and blending with MeOH—CHCl$_3$. After filtration, the extract was concentrated to yield a gum that was suspended in H$_2$O and extracted with n-hexane. After concentration, a portion of the oil obtained was chromatographed with n-hexane-acetone. Fractionation and purification of active components guided by our cytotoxicity assay resulted in the isolation of two novel, highly cytotoxic polyketide derived metabolites, plakortinic acid A (2, 8.0 mg, 0.01% yield), and its counterpart plakortinic acid B (3), along with known epiplakinic acid F (1, 170 mg, 0.21% yield), which had been isolated before from this sponge genus. Treatment of an aliquot of 3 with CH$_2$N$_2$ followed by successive CC and RP-HPLC yielded the methyl ester of plakortinic acid B (4, 12.0 mg, 0.02% yield), which was suitable for structure elucidation work. FIG. 4 shows the isolated polyketide-derived metabolites plakortinic acids A (2) and B (3) having a bicyclo[4.2.0]octene backbone. Although the presence of a major product was evident in the NMR spectra of 4, the existence of minor amounts (<25%) of another stereoisomer was detected as shown in FIG. 14-FIG. 19.

Experimental Section

General Experimental Procedures

Optical rotations were obtained with an Autopol IV automatic polarimeter. Infrared spectra were obtained with a Nicolet Magna FT-IR 750 spectrometer. 1D- and 2D-NMR spectra were recorded with a Bruker DRX-500 FTNMR spectrometer. Mass spectrometric data were generated at the Mass Spectrometry Laboratory of the University of Illinois at Urbana-Champaign. Column chromatography (CC) was performed using silica gel (35-75 mesh). TLC analysis was carried out using glass pre-coated silica gel plates, and the spots were visualized by exposure to I$_2$ vapor. All solvents used were either spectral grade or distilled from glass prior to use. Commercially available Diazald® and dimolybdenum tetraacetate were purchased from Sigma Aldrich Co.

Animal Material

Figure 1:
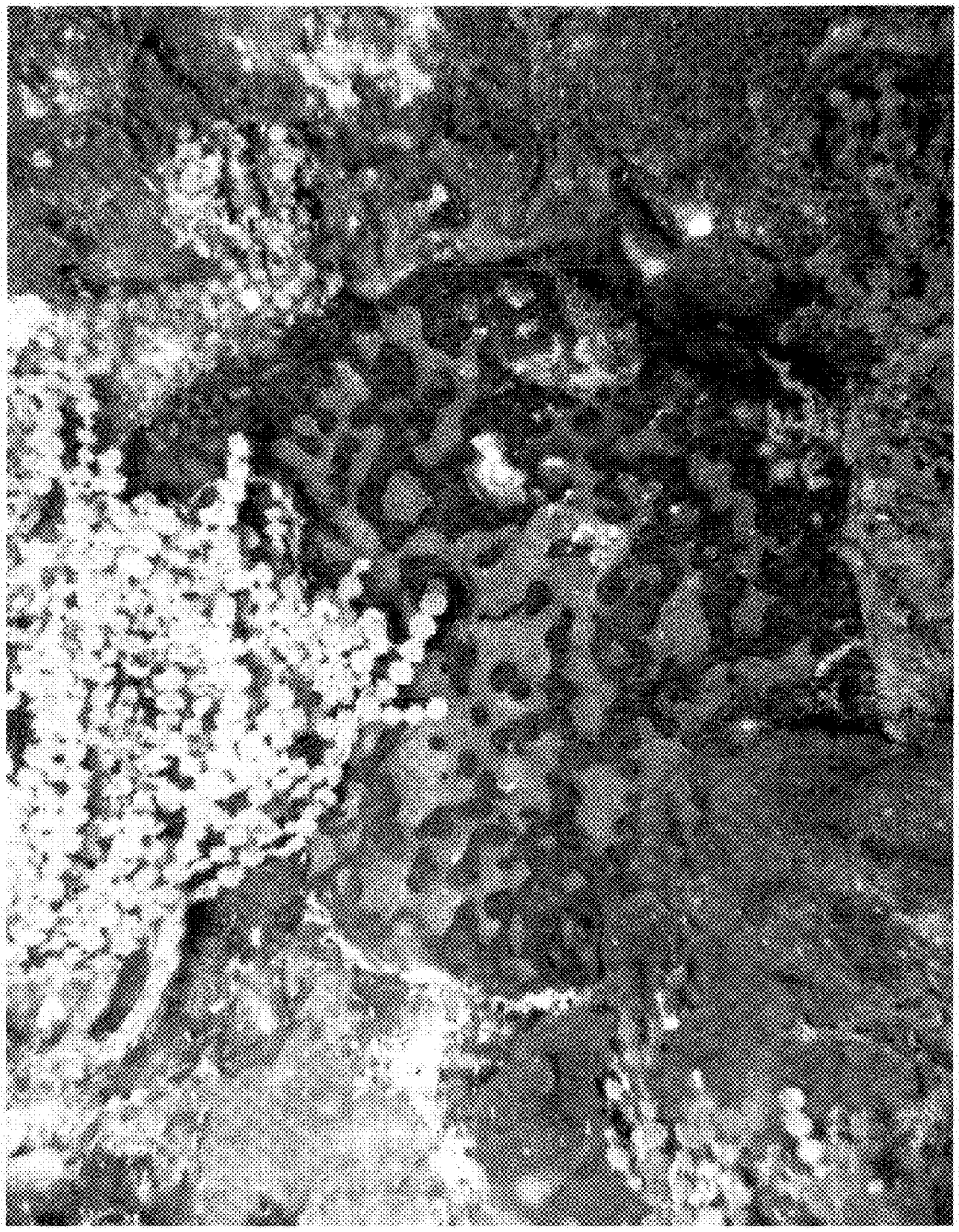
FIG. 1 shows an underwater photograph of the sponge consortium *Plakortis halichondrioides-Xestospongia deweerdtae*.
Figure 2A:
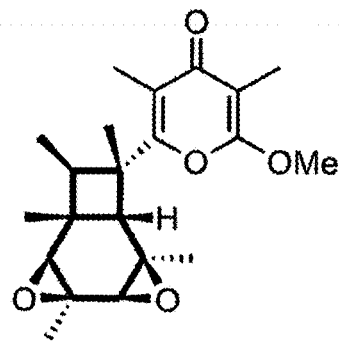
FIGS. 2a-2c show bicyclo[4.2.0]octane-based natural products of the prior art.
Figure 2A:
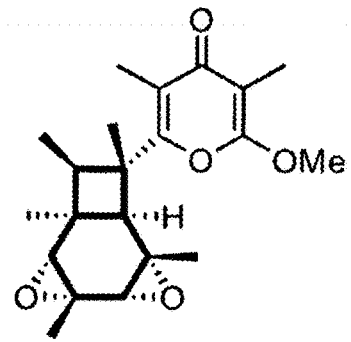
Figure 2B:
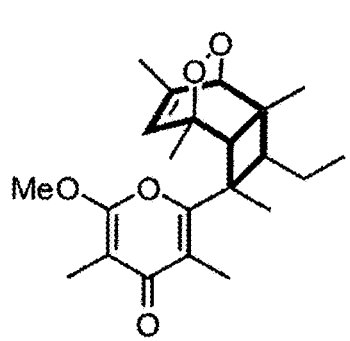
Figure 2B:
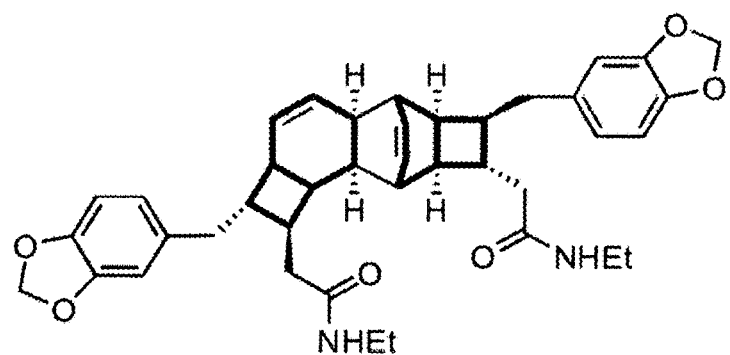
Figure 2B:
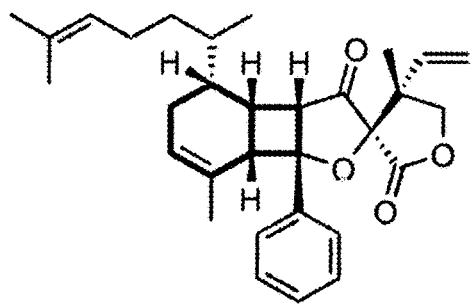
Figure 2B:
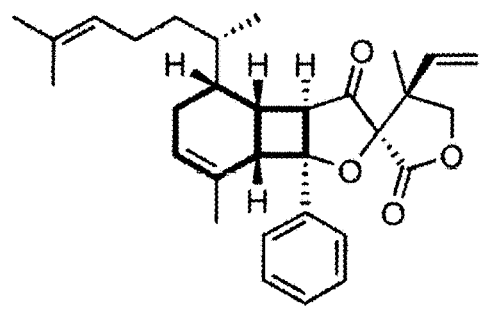
Figure 2C:
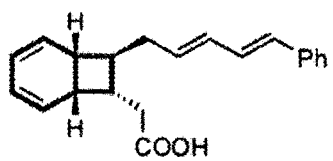
Figure 2C:
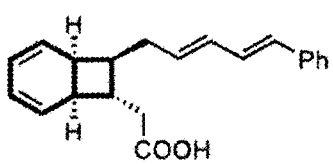
Figure 2C:
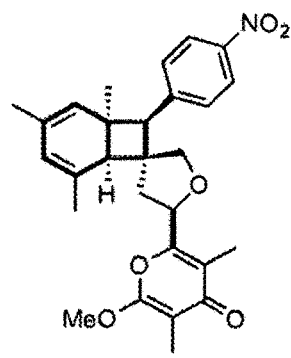
Figure 2C:
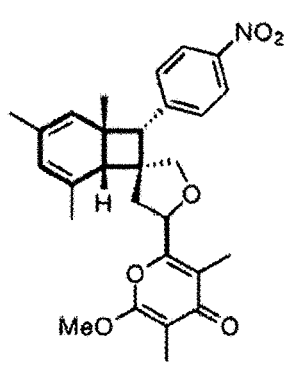
Figure 2C:
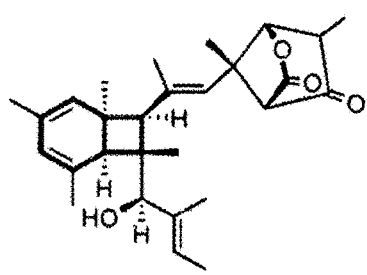
Figure 2C:
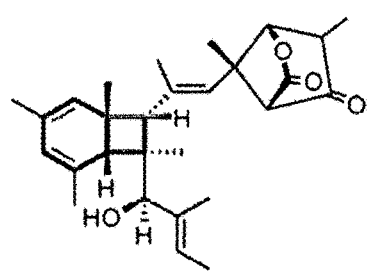
Figure 2C:
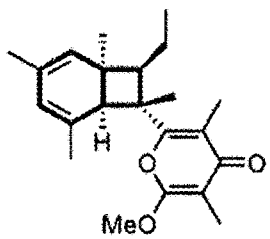
Figure 2C:
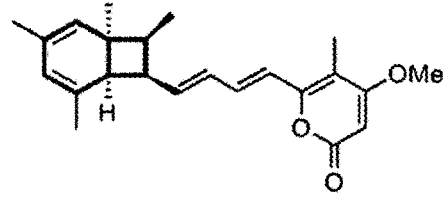
Figures 3A, 3B:
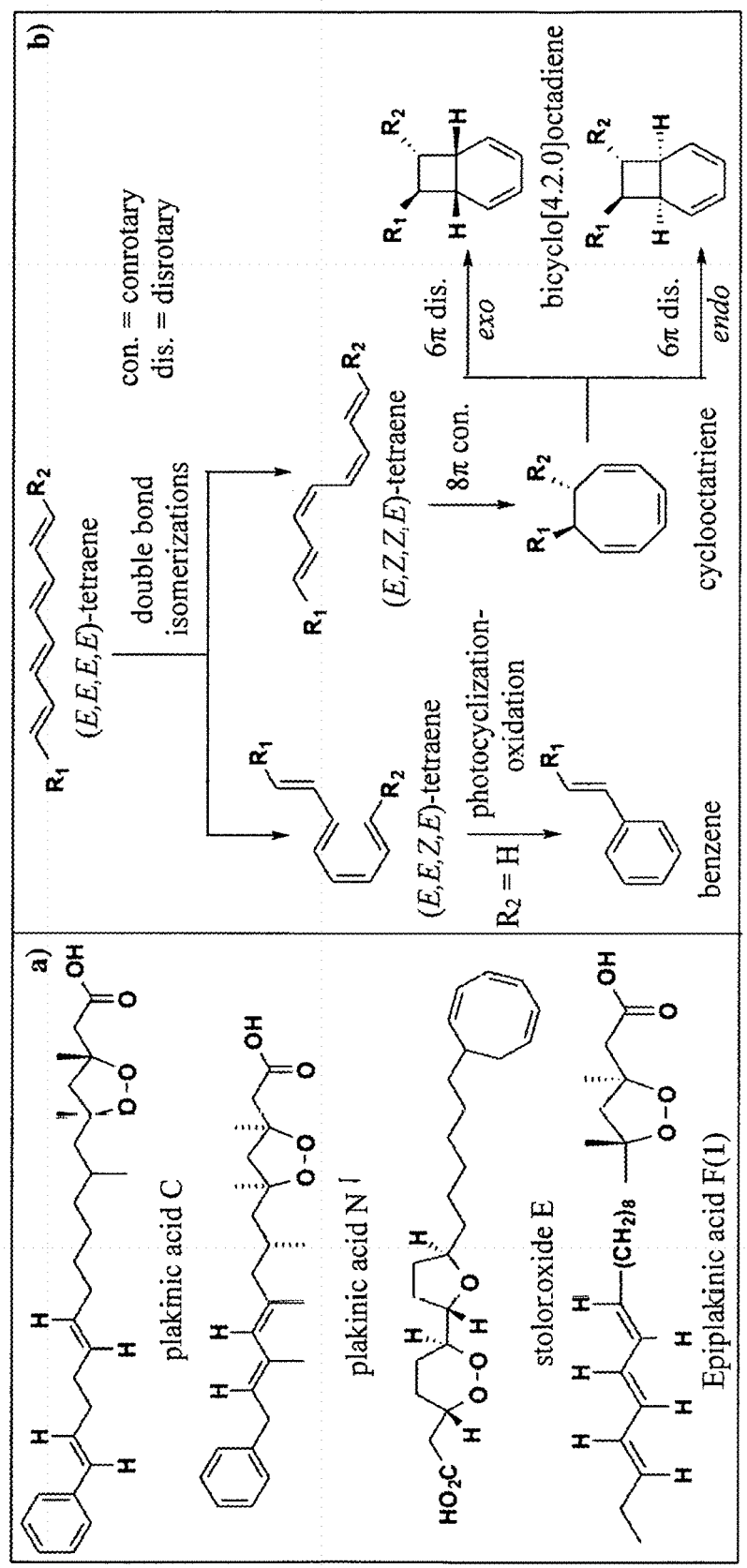
FIG. 3a shows previously reported marine natural products arising from a plausible biosynthetic pathway involving a polyene precursor.
FIG. 3b shows biogenetic proposals for the formation of the phenyl and bicyclo[4.2.0]octadiene motifs from a linear polyene precursor.

All individuals, found along the ceiling of cave overhangs with a drop shape, were massively encrusting with irregular conulose surface. Most specimens collected measured up to 20 cm long and 5 cm thick. All *Plakortis halichondrioides* colonies were overgrown with the thinly-encrusting sponge *Xestospongia deweerdtae*, which provides a lavender pink crust over the olive green color of *P. halichondrioides*. However, specimens turned to a brownish color, producing a dark exudate when brought to the surface. Individuals were easily broken, with firm consistency. Noticeable oscules along the surface were circular and measured 2.0-10.0 mm in diameter. The choanosome was compact with many cavities. Both choanosome and ectosome formed by high abundance of diods that were arranged homogenously and densely over the sponge body. Diods were curved with sharp edges. Straight triods with sharp edges were highly abundant. Nonetheless, many triods had rounded edges with a thick center. Triods and diods were variable in size. Minimum diod length varied from 110 to 160 µm, and the maximum actine length of triod length varied between 20 and 60 µm. The ectosome measured between 450 and 650 µm thick. A high density of unusual cavities formed a mesh that ran perpendicular to the surface of the ectosome. An underwater photograph of one of the sponge specimens is shown in FIG. 1.

Collection, Extraction, and Isolation

Fresh specimens of the sponge *Plakortis halichondrioides* (phylum Porifera; class Demospongiae; subclass Homoscleromorpha; order Homosclerophorida; family Plakinidae) were collected by hand using scuba at depths of 90-100 ft off Mona Island, Puerto Rico. A voucher specimen (No. IM06-09) is stored at the Chemistry Department of the University of Puerto Rico, Río Piedras Campus. The organism was frozen and lyophilized prior to extraction. The dry specimens (395 g) were cut into small pieces and blended in a mixture of CHCl$_3$-MeOH (1:1) (11×1 L). After filtration, the crude extract was concentrated and stored under vacuum to yield a dark gum (100 g), which was suspended in H$_2$O (2 L) and extracted with n-hexane (3×2 L), CHCl$_3$ (3×2 L), and EtOAc (3×2 L). Concentration under reduced pressure yielded 16.4 g of the n-hexane extract as a dark brown oil, a portion of which (3.7 g) was chromatographed over silica gel (130 g) using mixtures of n-hexane-acetone of increasing polarity (0-100%). A total of 11 fractions (I-XI) were generated on the basis of TLC and $^1$H NMR analysis. Further purification of fraction II (1.3 g) by silica gel (20.0 g) column chromatography in 2% acetone-n-hexane afforded eight sub-fractions, denoted as A-H. Purification of fraction B (659.1 mg) by silica gel (13.0 g) CC using CHCl$_3$ 100% as eluent afforded a mixture enriched with plakortinic acid B (3) (22 mg, 0.04% yield). The more polar fraction H (215 mg) was subjected to CC using reverse-phased silica gel (5 g) and eluted with a MeOH—H$_2$O gradient (6:4; 7:3; 8:2; 9:1; 1:0) to yield 7 sub-fractions denoted as H1-H7. Subfraction H4 (30 mg) was purified through a short plug of silica gel (0.8 g) with a CHCl$_3$-MeOH gradient (10:0; 9.5:0.5; 9:1) to afford plakortinic acid A (2) (8.0 mg, 0.01% yield). Purification of subfraction II (H) (659.1 mg) by silica gel (13.0 g) CC using CHCl$_3$ as eluent afforded the known epiplakinic acid F (1) (170 mg, 0.21% yield).

Methylation of Plakortinic Acid B (3)

To a solution of impure compound 3 (22 mg, 0.052 mmol) in CHCl$_3$ (8 mL) was added a solution of diazomethane in ether (10 mL), and the resulting mixture was stirred at 25° C. for 2 h. The oily residue obtained after concentration was chromatographed using a short plug of silica gel (1.0 g) and a mixture of n-hexane-acetone (95:5) to yield three fractions (I-III). Fraction II (15 mg) was submitted to reversed-phased HPLC chromatography (column: RP Analytical Hypersil 5µ C$_{18}$ 250×4.6 mm) using isocratic elution with MeCN—H$_2$O (85:15, flow rate: 0.80 mL/min). After HPLC purification, four sub-fractions were obtained (IIa-d). Subfraction IIc yielded compound 4 (12.0 mg, 53% yield) as an inseparable mixture in 3:1 ratio based on $^1$H NMR integration.

The present invention will be explained in conjunction with the NMR spectra shown in FIG. 6-21. Plakortinic acid A (2) was optically active and its molecular formula was determined as C$_{24}$H$_{40}$O$_6$ by HRESIMS (m/z 447.2726, [M+Na]$^+$, Δ +0.3 mDa) requiring 5 sites of unsaturation. Plakortinic acid A (2): colorless oil; [α]$_D^{20}$+28.5° (c 1.3, CHCl$_3$); IR (film) u$_{max}$ 3391, 2930, 2855, 1714, 1455, 1376, 1220, 1061 cm$^{-1}$; HRESIMS m/z [M+Na]$^+$447.2726 (calcd for C$_{24}$H$_{40}$O$_6$Na, 447.2723). The presence of hydroxyl and carboxylic acid groups was implied from the broad stretch at 3391 cm$^{-1}$ and sharp band at 1714 cm$_{-1}$, respectively. The $^1$C NMR spectra (Table 1 below) showed 24 resolved signals that, together with the $^{13}$C DEPT-135 and HSQC NMR data, were assigned as 4×CH$_3$, 9×CH$_2$, 7×CH, and 4×C; thus, compound 2 had to have 3 OH groups. The $^1$H NMR spectrum showed one olefinic proton ($\delta_H$ 5.56, d, J=5.8 Hz), two oxymethines ($\delta_H$ 4.11, dd, J=5.8, 3.3 Hz and 3.93, dd, J=9.7, 3.3 Hz), three methyl singlets ($\delta_H$ 1.65, 1.46, and 1.29), and one methyl triplet ($\delta_H$ 0.91, t, J=7.5 Hz). Some of these proton signals and those later ascribed to H$_2$-2 and H$_2$-4 were consistent with a 1,2-dioxolane bearing two methyl groups at C-3 and C-5 and an acetic group at C-3. All of the C—H correlations within 2 were established from a $^1$H-$^1$C HSQC experiment. HMBC cross-peaks of H$_2$-2 with C-1, C-3, and C-22 and of H$_2$-4 with C-3, C-5, C-6, C-22, and C-23, confirmed that 2 contained the same free 1,2-dioxolane carboxylic acid as epiplakinic acid F (1). $^1$H-$^1$H COSY correlations of H-16-H-15-H-14-H-13-H-12-H-19-H-18-H-13, along with the key HMBC correlations of H-18 ($\delta_H$ 2.34, t, J=8.4 Hz) with C-13, C-14, C-16, C-17, C-19, C-20, and C-24 and of H-13 ($\delta_H$ 2.41) with C-12, C-14, and C-18 led us to a bicyclo[4.2.0]octene ring system for plakortinic acid A (2). COSY, HMQC, and HMBC data routinely established the spin systems from H$_2$-11 through H-16, H-18 through H$_3$-21, including H-13 and H-18 and those of H-12/H19. These correlations also helped us establish unequivocally the locus of the 1,2-diol array at C-14/C-15. Furthermore, the HMBC correlation of H$_3$-21 ($\delta_H$ 0.91, t, J=7.5 Hz) with C-19 and C-20 allowed us to attach an ethyl group to C-19. Based on these observations, we concluded that the remaining NMR signals had to be those of a straight alkyl side chain (C6 through C11) connecting the bicyclo[4.2.0]octene and cycloperoxide ring units.

TABLE 1

NMR Spectroscopic Data for 2 in CDCl$_3$

| position | $\delta_C^a$ | $\delta_H^b$ (J in Hz) | HMBC (H→C#) |
|---|---|---|---|
| 1 | 174.5, C | | |
| 2a | 43.9, CH$_2$ | 2.76, d (14.8) | 1, 3, 4, 22 |
| 2b | | 2.72, d (14.8) | 1, 3, 4, 22 |
| 3 | 83.9, C | | |
| 4a | 55.7$^c$, CH$_2$ | 2.25, d (12.5)$^c$ | 2, 3, 5, 6, 7, 22, 23 |
| 4b | | 2.44, d (12.5)$^c$ | 2, 3, 5, 6, 22, 23 |
| 5 | 86.6$^c$, C | | |
| 6ab | 39.5, CH$_2$ | 1.70, m; 1.53, m | 7 |
| 7ab | 24.3$^c$, CH$_2$ | 1.38, m; 1.30, m | |
| 8 | 29.8c, CH$_2$ | 1.30, m | |
| 9 | 29.7, CH$_2$ | 1.30, m | |
| 10ab | 28.2$^c$, CH$_2$ | 1.39, m; 1.28, m | |
| 11ab | 30.7, CH$_2$ | 1.58, m; 1.38, m | 9, 12 |
| 12 | 39.8f, CH | 2.03, m | 20 |
| 13 | 35.6$^c$, CH | 2.41, q (8.9 Hz) | 12, 14, 18, 19 |
| 14 | 68.9$^c$, CH | 3.93, dd (9.7, 3.3) | 12, 13 |
| 15 | 67.8, CH | 4.11, dd (5.8, 3.3) | 13, 14, 16, 17 |
| 16 | 121.3, CH | 5.56, d (5.8) | 14, 15, 18, 24 |
| 17 | 143.1, C | | |
| 18 | 42.1, CH | 2.34, t (8.4) | 13, 14, 16, 17, 19, 20, 24 |
| 19 | 49.2, CH | 1.66, m | 12, 18, 21 |
| 20ab | 28.8, CH$_2$ | 1.58, m; 1.49, m | 12, 18, 19, 21 |
| 21 | 11.9, CH$_3$ | 0.91, t (7.5) | 19, 20 |
| 22 | 23.8, CH$_3$ | 1.46, s | 2, 3, 4 |
| 23 | 23.2$^c$, CH$_3$ | 1.29, s | 4, 5, 6, 7 |
| 24 | 21.3, CH$_3$ | 1.65, s | 16, 17, 18 |

$^a$Recorded at 125 MHz. Multiplicities were obtained from a DEPT-135 experiment.
$^b$Recorded at 500 MHz.
$^c$Two sets of signals with partial overlap)

The relative configurations of the stereocenters of the strained ring systems in plakortinic acid A (2) were established on the basis of correlations in the NOESY NMVR spectrum as well as through interpretation of NMVR coupling constant data (Table 1). The H$_2$-4 proton ($\delta_H$ 2.44) that is cis to the acetic acid side chain appears downfield from the proton trans to the acetic acid. Thus, H-4b showed strong dipolar coupling to H$_3$-23. H-4a ($\delta_H$ 2.25) showed strong dipolar couplings to H$_3$-22 and H$_2$-6. All of these are consistent with a trans relative stereochemistry for the 1,2-dioxolane carboxylic acid moiety of 2. The assignments shown in 2 of C-3 and C-5 are not arbitrary. Rather, they are based on nearly identical NMR and [α]$_D$ data plus the NOESY experiments which showed correlations identical to those reported for the co-isolated known compound 1. Cross-peaks of H-13 with H-12 and H-18, and of H-12 with H$_3$-21 placed these protons on the same face of the bicyclo ring system. Due to the near coincidence in chemical shifts between H-13 and H-18 in CDCl$_3$, no consideration about their relative orientation could be established on the basis of NOESY experiments. However, in Bz-d$_6$ greater dispersion in the chemical shifts made it possible to detect an NOE cross-peak between these nuclei. While those of H-14 with H$_2$-11, H-15, and H-19 were used to place them on the opposite face. The conspicuous absence of NOE's between H-19, H-12, and H-18 confirmed their trans quasi-diaxial relationship. The coupling constant for H-13 and H-14 (J=9.7 Hz) is in full agreement with their trans-diaxial orientation, whereas the small coupling constant between H-14 and H-15 (J=3.3 Hz) supports the cis geometry for the 1,2-diol array in 2. Therefore, the relative configuration of plakortinic acid A (2) was determined to be 3S*, 5R*, 12S*, 13S*, 14R', 15S*, 18R', 19S*. An attempt to assign the absolute configuration of the 14,15-diol moiety in 2 using the dimolybdenum CD method was unsuccessful as the CD spectrum did not display a measurable Cotton effect.

Plakortinic acid B methyl ester (4) was obtained also as an optically active substance. Plakortinic acid B methyl ester (4): colorless oil; [α]$_D$$^{20}$=+12.6° (c 0.54, CHCl$_3$); IR (film) u$_{max}$ 2932, 2854, 1738, 1456, 1376, 1210, 1088, 1012, 715 cm$^{-1}$; HRESIMS m/z [M+H]+437.2910 (calcd for C$_{25}$H$_{40}$O$_6$, 437.2903). Its HRESIMS indicated a [M+H]$^+$ ion peak at m/z 437.2910, suggesting a molecular formula of C$_{25}$H$_{40}$O$_6$, from which 6 degrees of unsaturation could be deduced. The $^{13}$C NMR and DEPT-135 NMR spectra (Table 2) exhibited 25 signals for 5 methyl, 9 methylene, 7 methine, and 4 quaternary carbons. The 1D and 2D NMR spectra of 4 revealed strong structural analogies with compound 2, suggesting the presence of the same carbon skeleton. However, in place of a cyclohex-3-ene-1,2-diol system, compound 4 was characterized by a methine linked to an oxygen atom ($\delta_H$ 4.63, H-14; $\delta_c$ 72.5, C-14), an oxygenated tertiary sp$^3$ carbon at $\delta_c$ 77.3 (C-17), and a 1,2-disubstituted double bond [$\delta_H$ 6.76 (H-15), 6.34 (H-16); $\delta_c$ 132.6 (C-15), 135.8 (C-16)]. According to these data, a peroxide bridge across C-14/C-17 was suggested for compound 4. Conceivably, compound 3 could be an artifact formed during work-up via 1,4-addition of O$_2$ to a bicyclo[4.2.0]octadiene precursor. The remaining part of the molecule was the same as 2. All proton and carbon resonances were attributed as reported in Table 2 by detailed NMR analysis ($^1$H-$^1$H COSY, HSQC, and HMBC).

Figure 22:
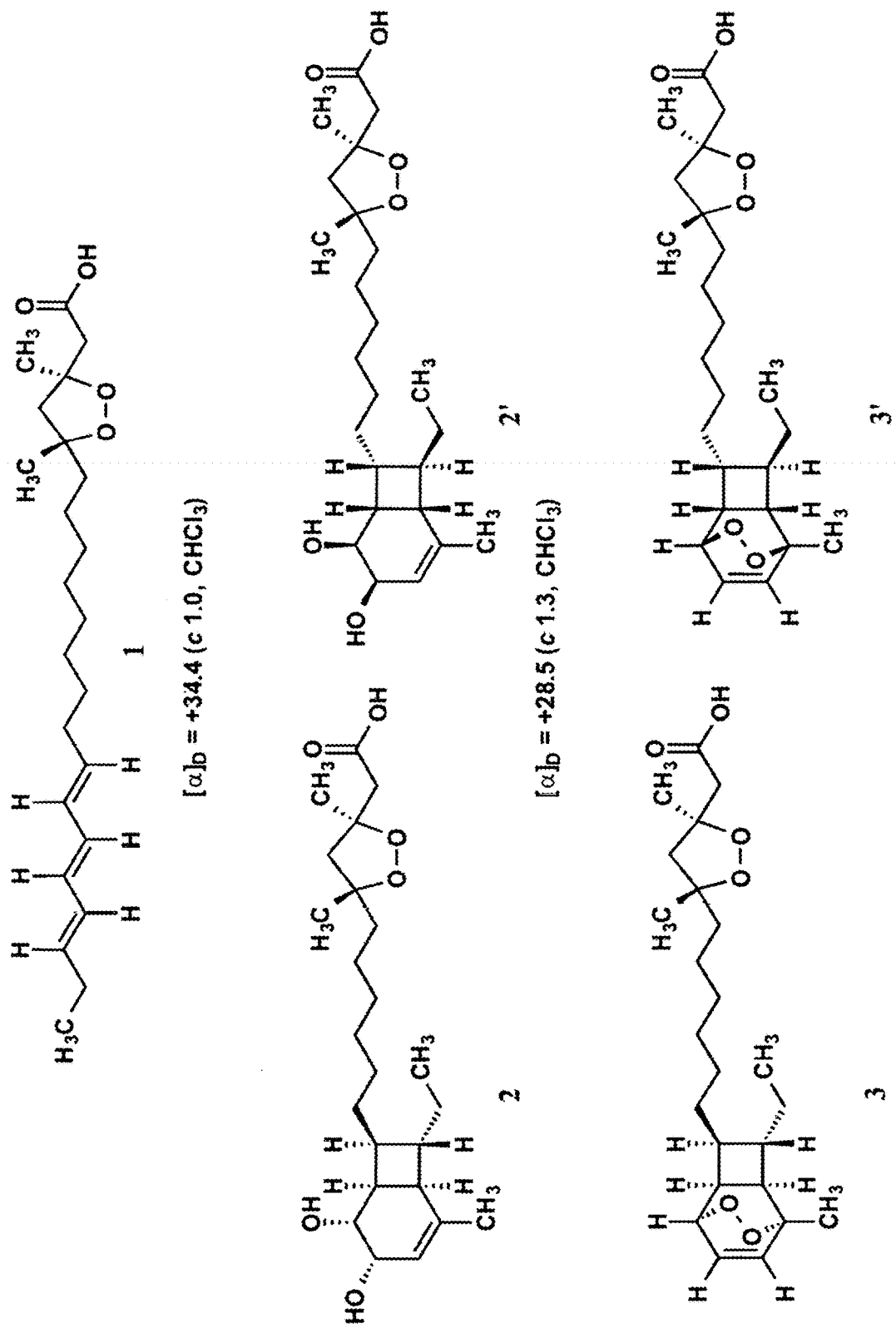
FIG. 22 shows suggested rationales for the NMR resonances that are observed in pairs in compound (2) and (4), according to the present invention.

In spite of their structural dissimilarities, epiplakinic acid F (1) and plakortinic acid A (2) have [α]$_D$ values of the same positive sign and similar magnitudes. Although this could be dismissed as a coincidence, it might also imply that plakortinic acid A actually consists of an inseparable mixture of two diastereomers, namely, 2 (3S*, 5R*, 12S*, 13S*, 14R*, 15S*, 18R*, 19S*) and 2' (3S*, 5R*, 12R*, 13R*, 14S*, 15R*, 18S*, 19R*). In order to account for this interpretation, as shown in FIG. 22, we propose that the bicyclic backbone of plakortinic acid A (2) is formed spontaneously, i.e., without the assistance of enzymes, from an achiral tetraene precursor through 8π-6π electrocyclization cascades as racemates (note: natural products whose biosynthesis involves an 8π-6π electrocyclization cascade are typically isolated as racemates). Additional reactions (hereon assisted by enzymes) would then ensue leading to the 1,2-dioxolane unit. We surmise that the specific rotation of the inferred 1:1 mixture of diastereomers (2 and 2') is set exclusively by the dominant influence of a chiral 1,2-dioxolane of well-defined configuration (3S,5R), and that any contributions to $[\alpha]_D$ arising from the bicyclo[4.2.0] octene systems cancel out. This hypothesis is supported by the fact that, although compound 2 consistently behaved as a pure compound during multiple chromatographic analyses (TLC, CC, HPLC), a handful of NMR signals (in particular those ascribable to the 1,2-dioxolane array) were observed as pairs. This phenomenon appears to heighten in Bz-$d_6$ solution. This hypothesis could also explain why we were not able to establish the absolute configuration of the 14,15-diol array in plakortinic acid A using the in situ dimolybdenum CD method developed by Frelek. On the basis of this rationale, we also propose that plakortinic acid B was isolated as an inseparable 3:1 mixture of isomers 3 and 3' (the assignment of structures is arbitrary).

As a second rationale, as mentioned earlier, in the case of plakortinic acid A, the initial characterization by $^1$H and $^{13}$C NMR was complicated because of the duplication of some of the proton and carbon signals. Conceivably, rotation around the straight alkyl chain gives rise to (at least) two quickly interchanging rotational isomers with subtle different chemical shift values in a ratio of approximately 1:1. Unfortunately, we did not try to confirm this phenomenon by running the experiments in DMSO-$d_6$ (with the hope of observing the coalescence of the duplicating peaks). Rotational isomerization is a reasonable rationale given the inherent conformational flexibility introduced by the —(CH$_2$)$_6$— bridge of 2 and 3.

TABLE 2

NMR Spectroscopic Data for 4 in CDCl$_3$

| position | $\delta_c{}^a$ | $\delta_H{}^b$ (J in Hz) | HMBC (H→C#) |
|---|---|---|---|
| 1 | 171.1 C | | |
| 2a | 44.0, CH$_2$ | 2.76, d (14.5) | 1, 3, 4, 22 |
| 2b | | 2.65, d (14.5) | 1, 3, 4, 22 |
| 3 | 83.9, C | | |
| 4a | 55.4, CH$_2$ | 2.22, d (12.6) | 2, 3, 5, 6, 22 |
| 4b | | 2.47, d (12.6) | 2, 3, 5, 6, 23 |
| 5 | 86.4, C | | |
| 6ab | 39.6, CH$_2$ | 1.69 m; 1.52, m | |
| 7 | 24.4, CH$_2$ | 1.32, m | |
| 8 | 29.6, CH$_2$ | 1.25, m | |
| 9 | 29.6, CH$_2$ | 1.25, m | |
| 10 | 28.3, CH$_2$ | 1.13, m | |
| 11 | 30.7, CH$_2$ | 1.35, m | |
| 12 | 31.3, CH | 2.04, m | 11, 13, 14 |
| 13 | 35.2, CH | 3.04, ddd (9.2, 9.0, 4.8) | 14, 18 |
| 14 | 72.5, CH | 4.63, t (5.3) | 13, 15, 16, 18 |
| 15 | 132.6, CH | 6.76, dd (8.1, 6.2) | 13, 14, 17 |
| 16 | 135.8, CH | 6.34, d (8.1) | 14, 17, 18, 24 |
| 17 | 77.3, C | | |
| 18 | 42.5, CH | 2.30, dd (8.3, 5.8) | 13, 16, 17, 20, 24 |
| 19 | 44.8, CH | 1.52, m | 12, 17, 20 |
| 20ab | 29.9, CH$_2$ | 1.38, m; 1.28, m | 21 |
| 21 | 11.9, CH$_3$ | 0.81, t (7.3) | 19, 20 |
| 22 | 24.1, CH$_3$ | 1.43, s | 2, 3, 4 |
| 23 | 23.2, CH$_3$ | 1.28, s | 4, 5, 6 |
| 24 | 20.5, CH$_3$ | 1.32, s | 16, 17, 18 |
| —OCH$_3$ | 51.7, CH$_3$ | 3.69, s | 1 |

$^a$Recorded at 125 MHz. Multiplicities were obtained from a DEPT-135 experiment.
$^b$Recorded at 500 MHz The relative stereochemistry of compound 4, suggested by comparison of their proton and carbon chemical shifts, was based mainly on NOESY experiments. The expected cis geometry of the 13,18 junction was suggested by a diagnostic NOE effect between the angular methines at those sites. The peroxide bridge was α-oriented with respect to the plane of the bicyclo[4.2.0]octene by the downfield shift of H-13, which in compound 4 resonated at δ 3.04 vs δ 2.41 of 2, suggesting that both the peroxide unit and the angular methine at C-13 were on the same side of the molecule. Additional NOE's, particularly H-16/H-19, H$_2$-11/H-15, H-12/H-13 and H-18/H$_3$-21 fixed the relative stereochemistry shown in 4.

Figure 5:
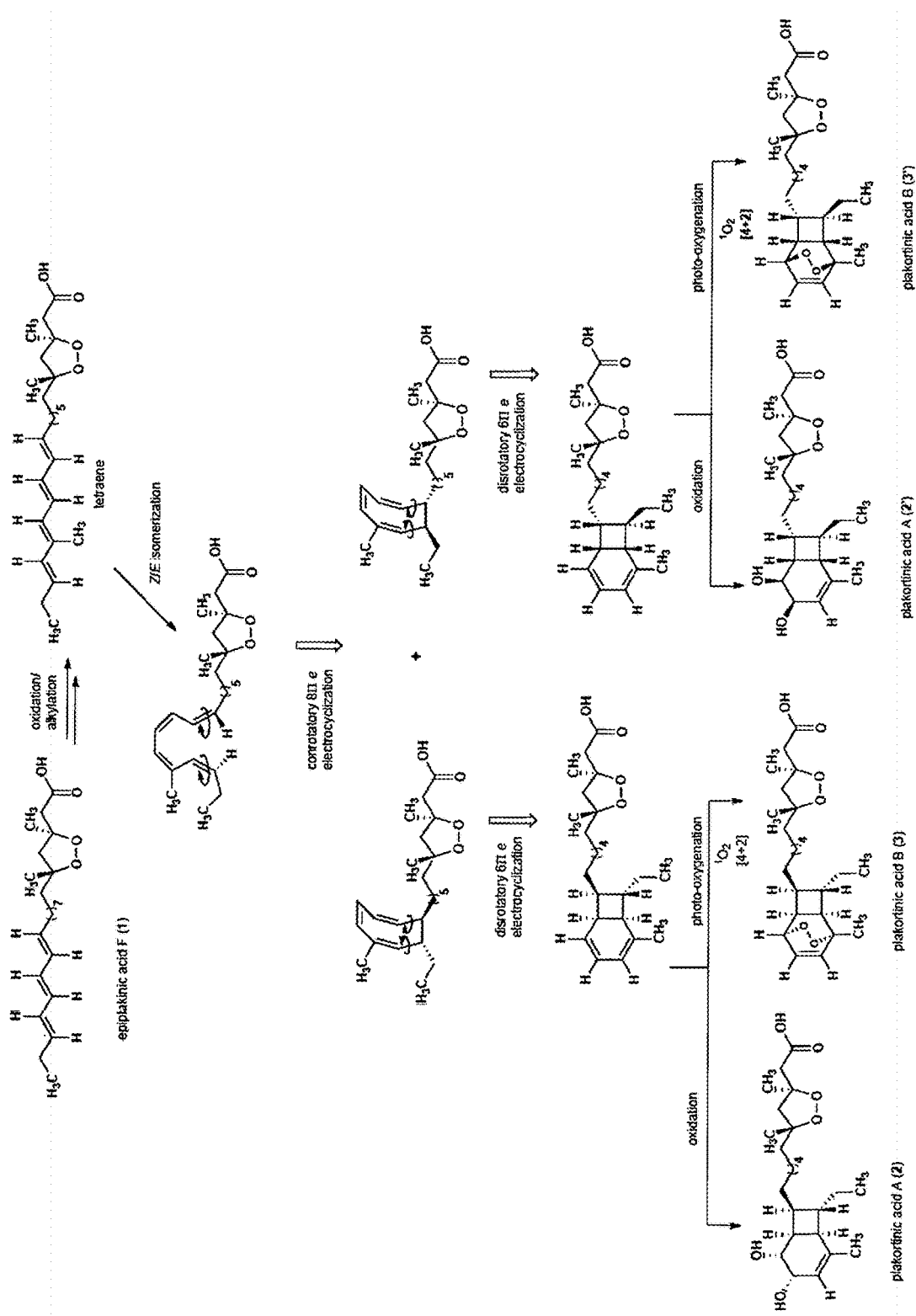
FIG. 5 shows a plausible biogenetic pathway of plakortinic acids A (2) and B (3) from epiplakinic acid F (1).
Figure 6:
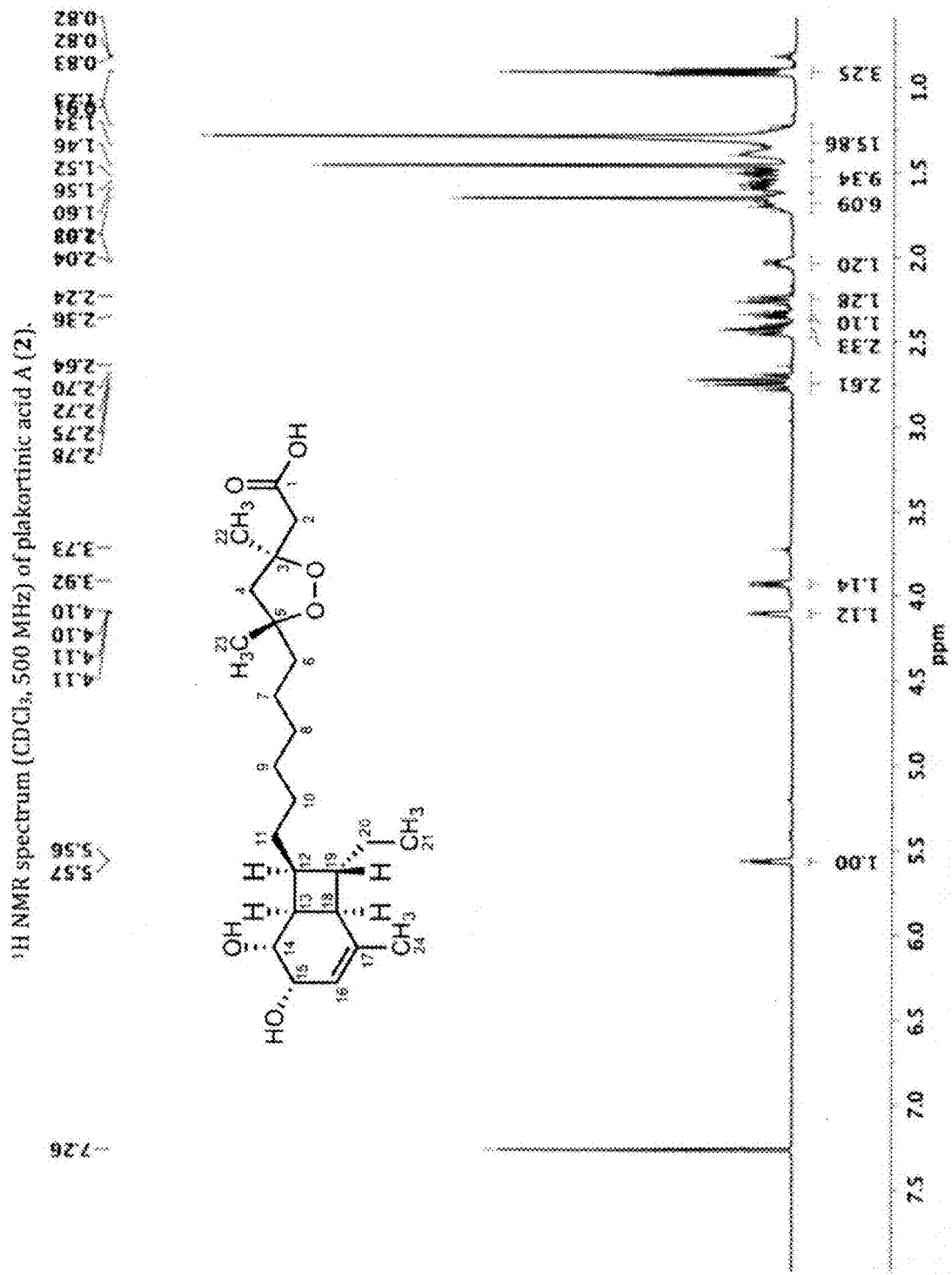
FIG. 6 shows $^1$H NMR spectrum (CDCl$_3$, 500 MHz) of plakortinic acid A (2), according to the present invention.
Figure 7:
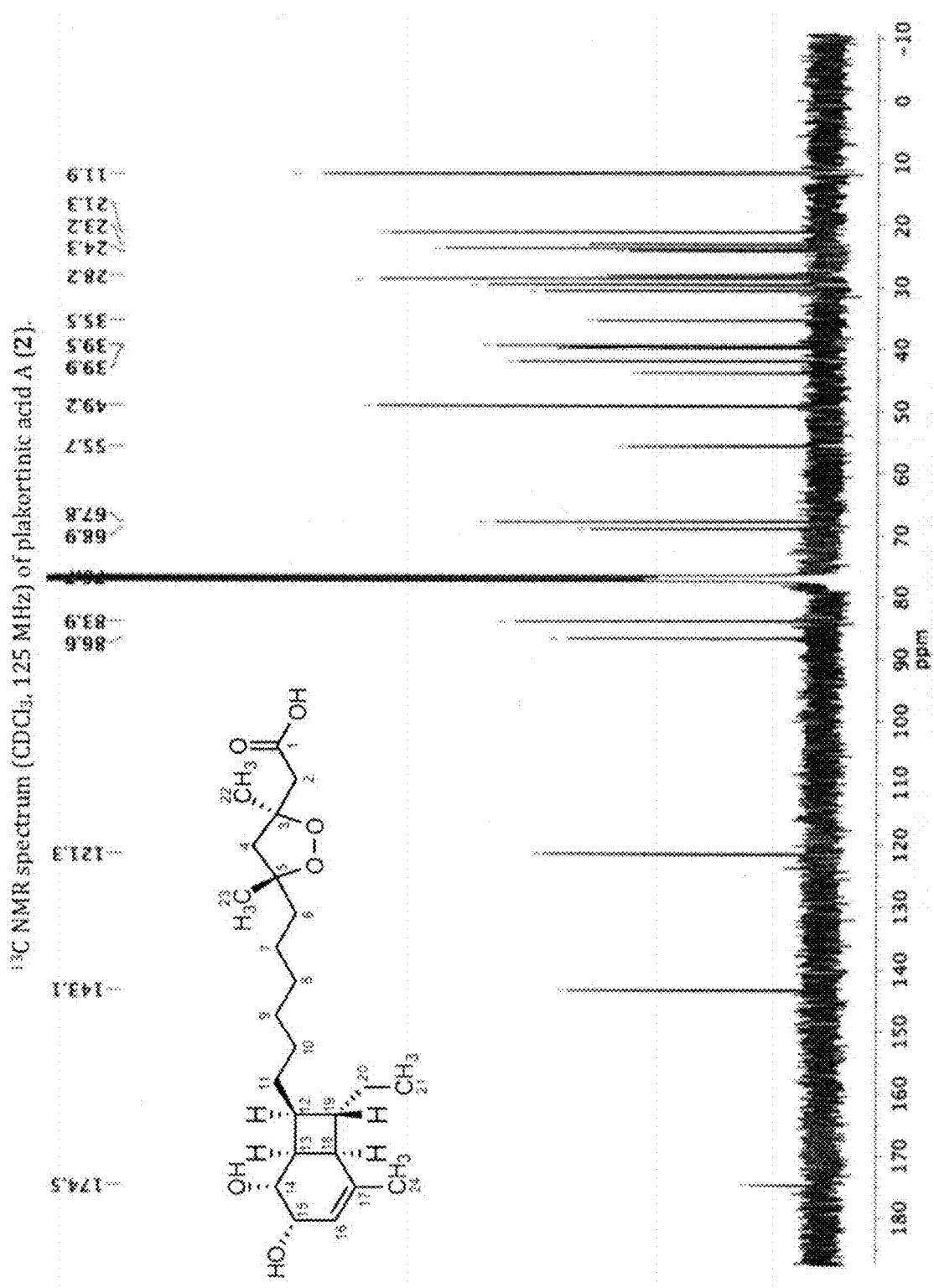
FIG. 7 shows $^{13}$C NMR spectrum (CDCl$_3$, 125 MHz) of plakortinic acid A (2), according to the present invention.
Figure 8:
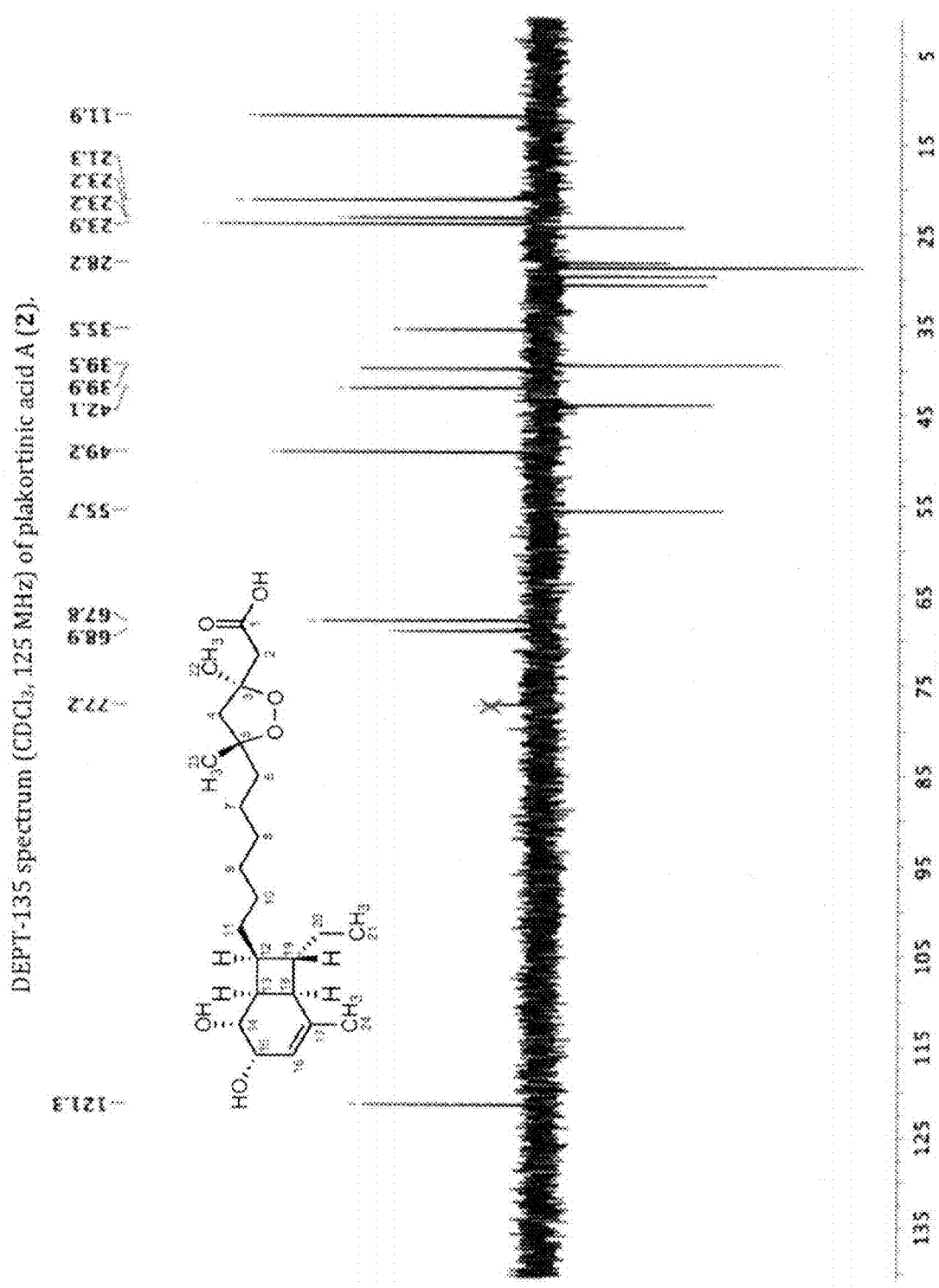
FIG. 8 shows DEPT-135 spectrum (CDCl$_3$, 125 MHz) of plakortinic acid A (2), according to the present invention.
Figure 9:
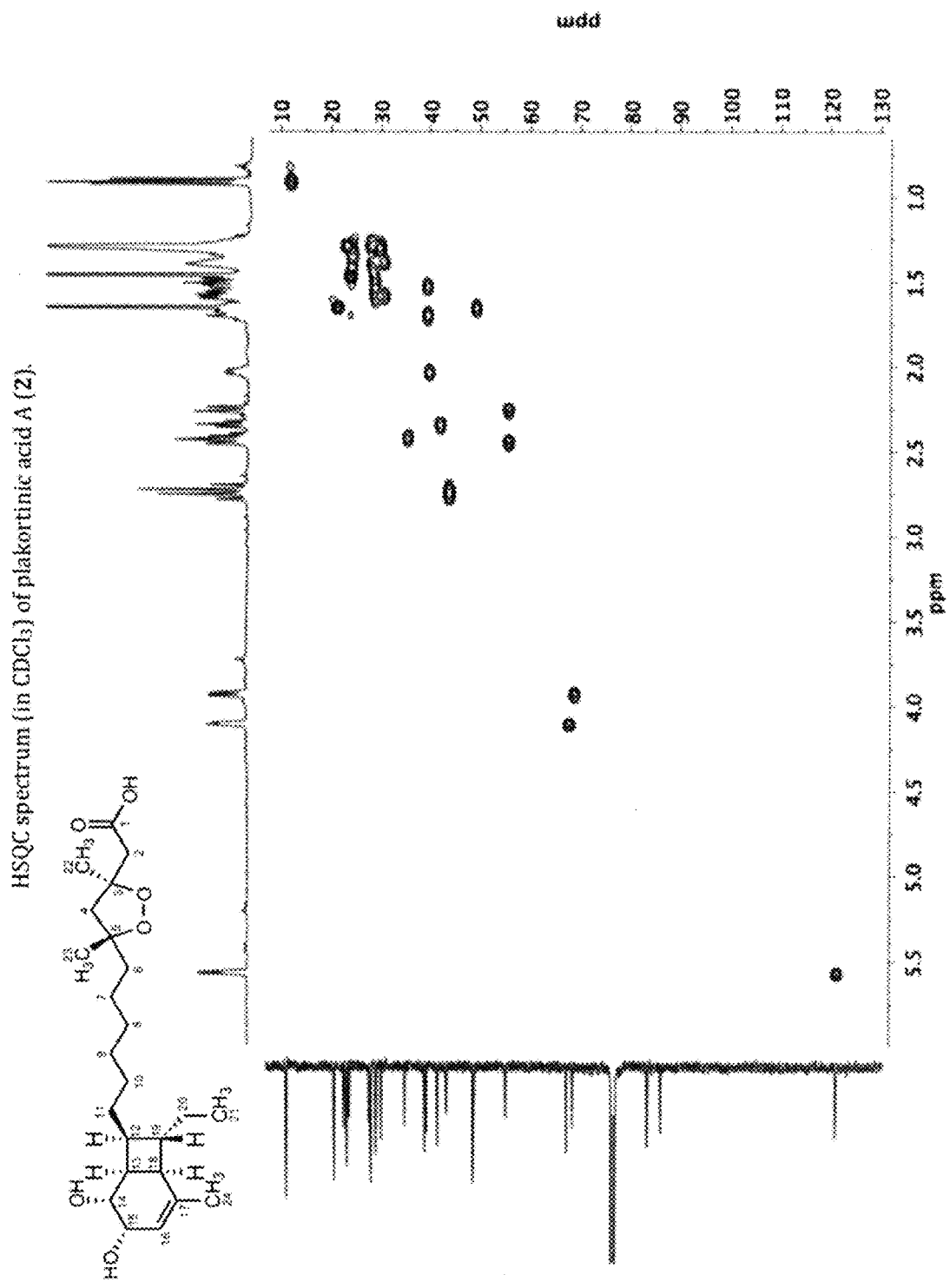
FIG. 9 shows HSQC spectrum (in CDCl$_3$) of plakortinic acid A (2), according to the present invention.
Figure 10:
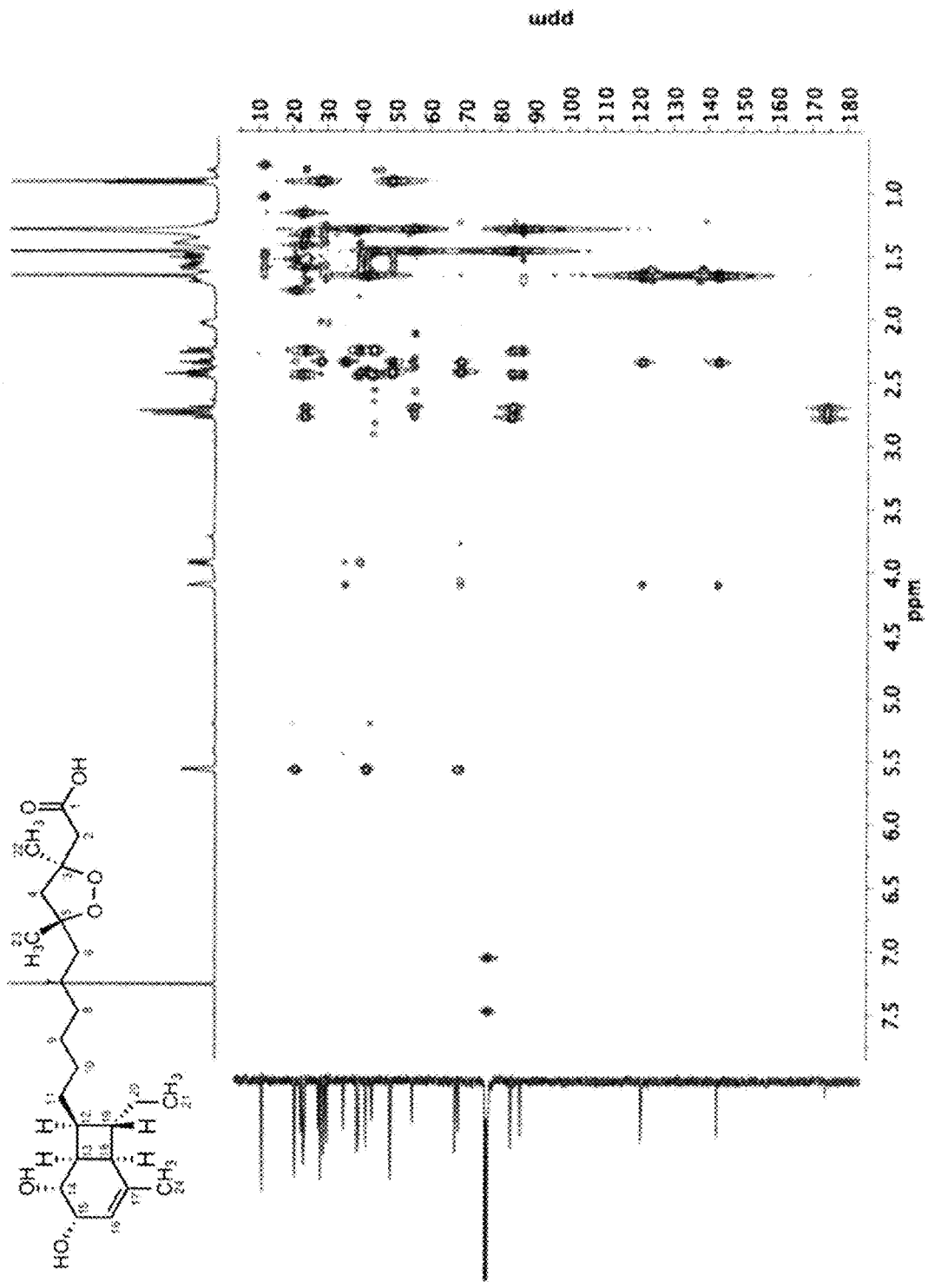
FIG. 10 shows HMBC spectrum (in CDCl$_3$) of plakortinic acid A (2), according to the present invention.
Figure 11:
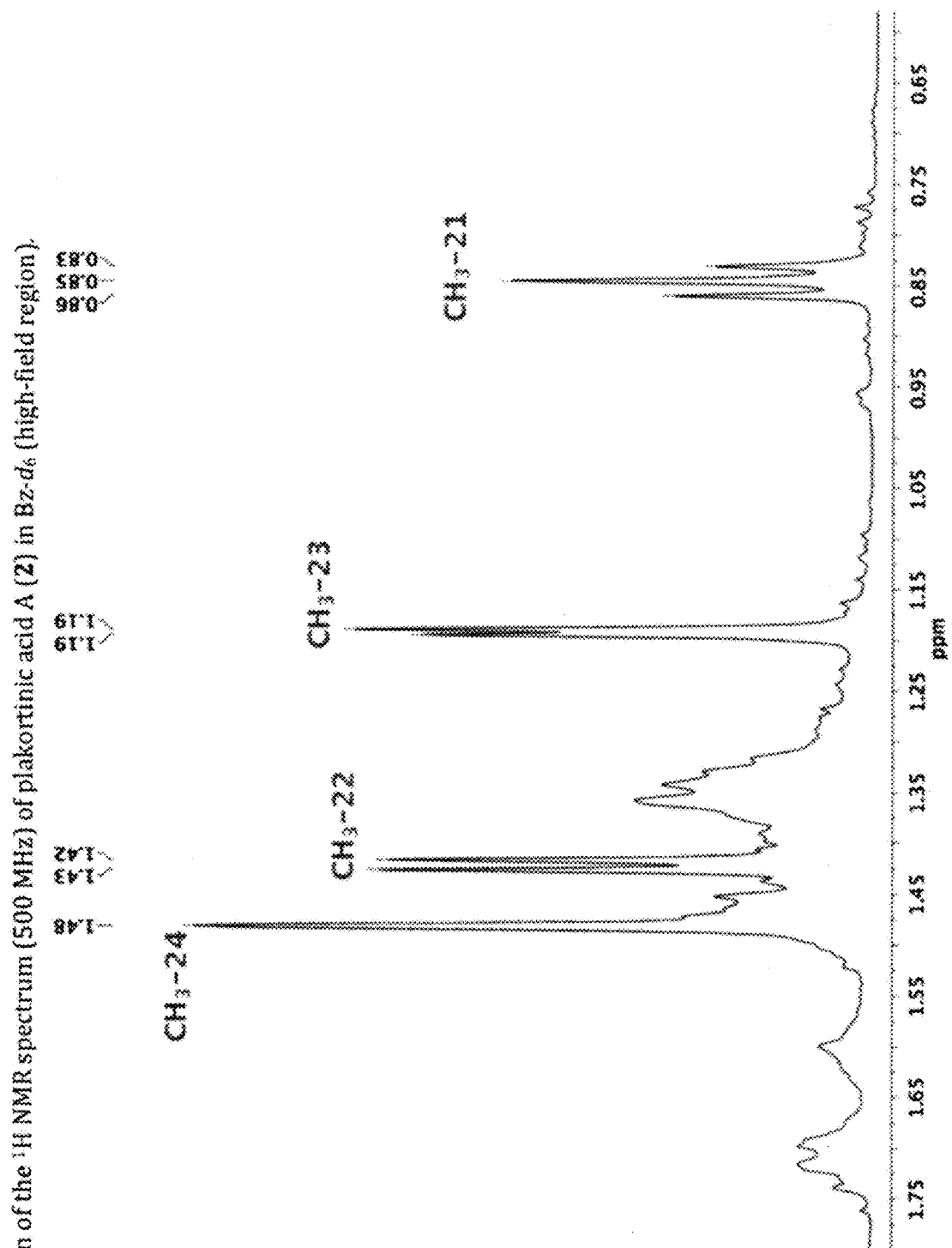
FIG. 11 shows expansion of the $^1$H NMR spectrum (500 MHz) of plakortinic acid A (2) in Bz-d$_6$ (high-field region), according to the present invention.
Figure 12:
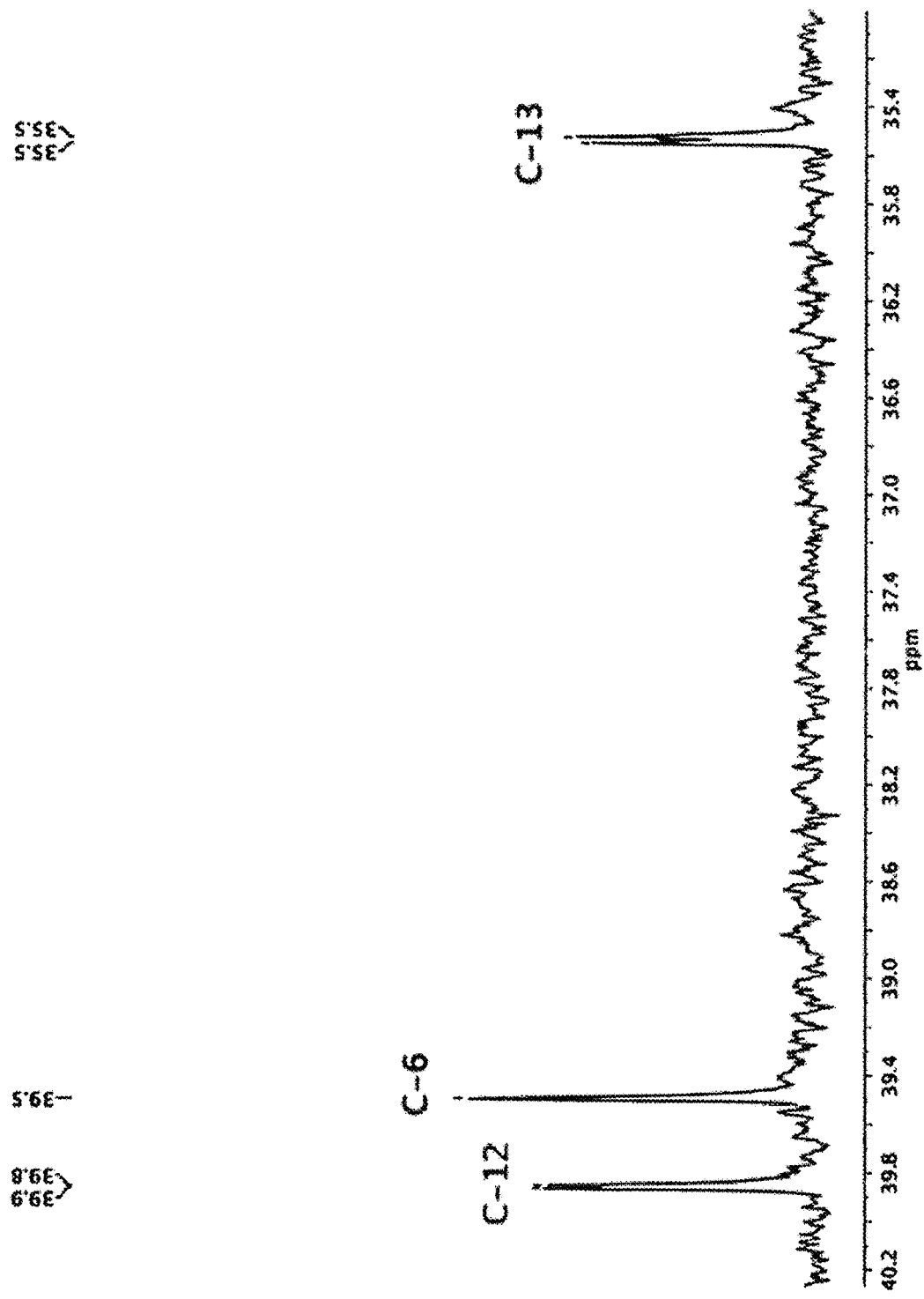
FIG. 12 shows expansion of the $^{13}$C NMR spectrum (125 MHz) of plakinic acid A (2) in CDCl$_3$, according to the present invention.
Figure 13:
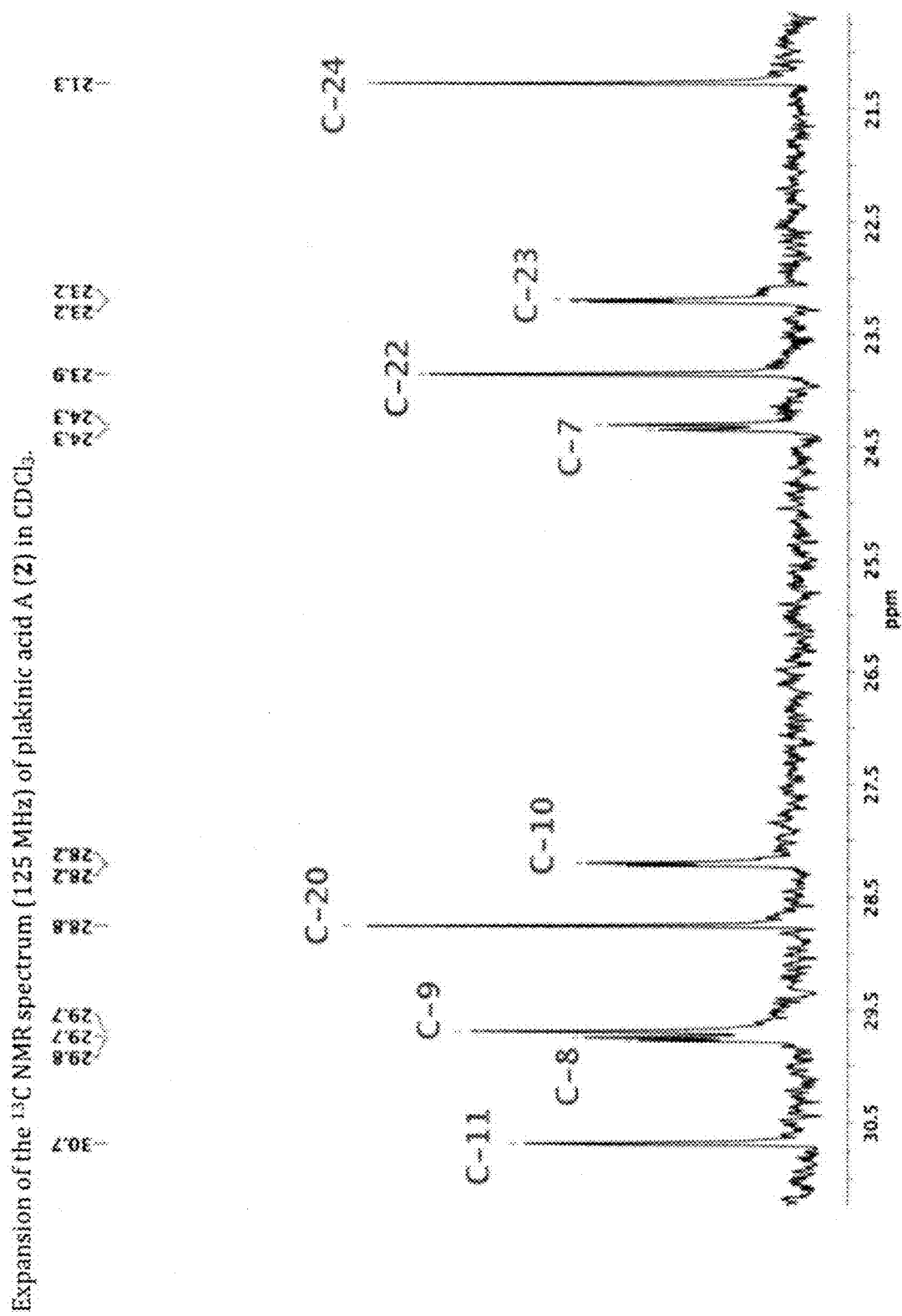
FIG. 13 shows expansion of the $^{13}$C NMR spectrum (125 MHz) of plakinic acid A (2) in CDCl$_3$, according to the present invention.
Figure 14:
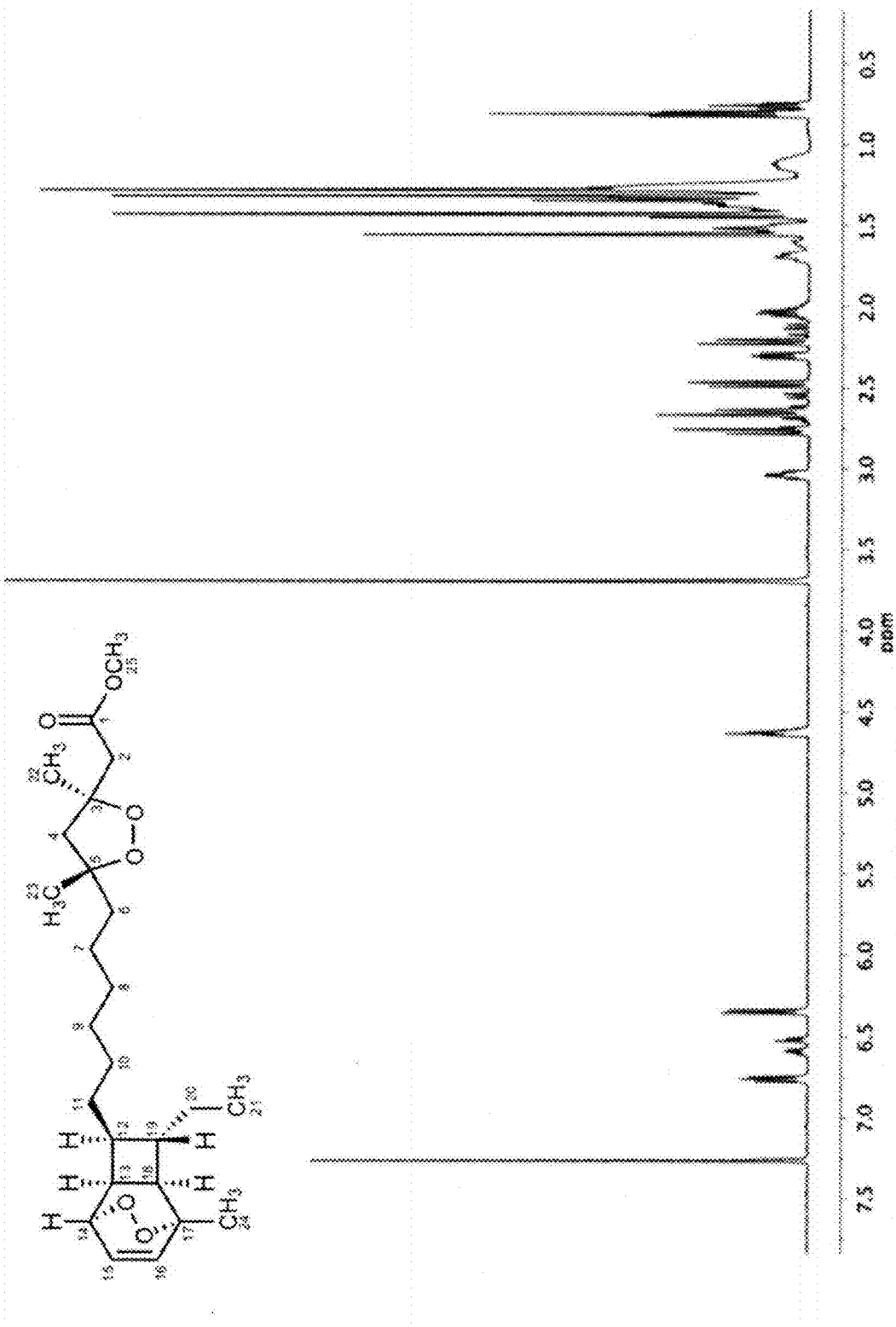
FIG. 14 shows $^1$H NMR spectrum (CDCl$_3$, 500 MHz) of plakortinic acid B methyl ester (4), according to the present invention.
Figure 15:
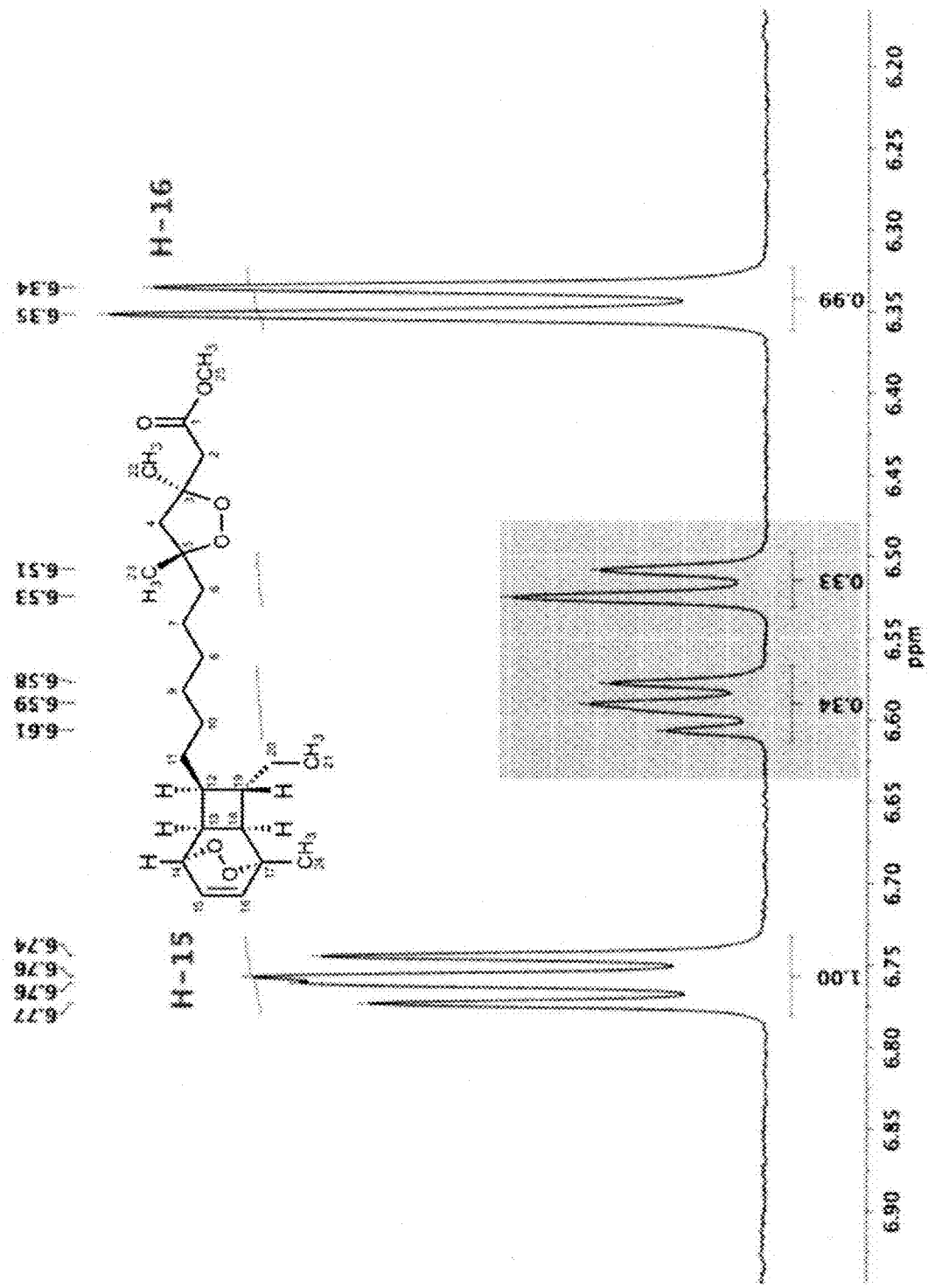
FIG. 15 shows a low field region of the $^1$H NMR spectrum (CDCl$_3$, 500 MHz) of compound (4), according to the present invention.
Figure 16:
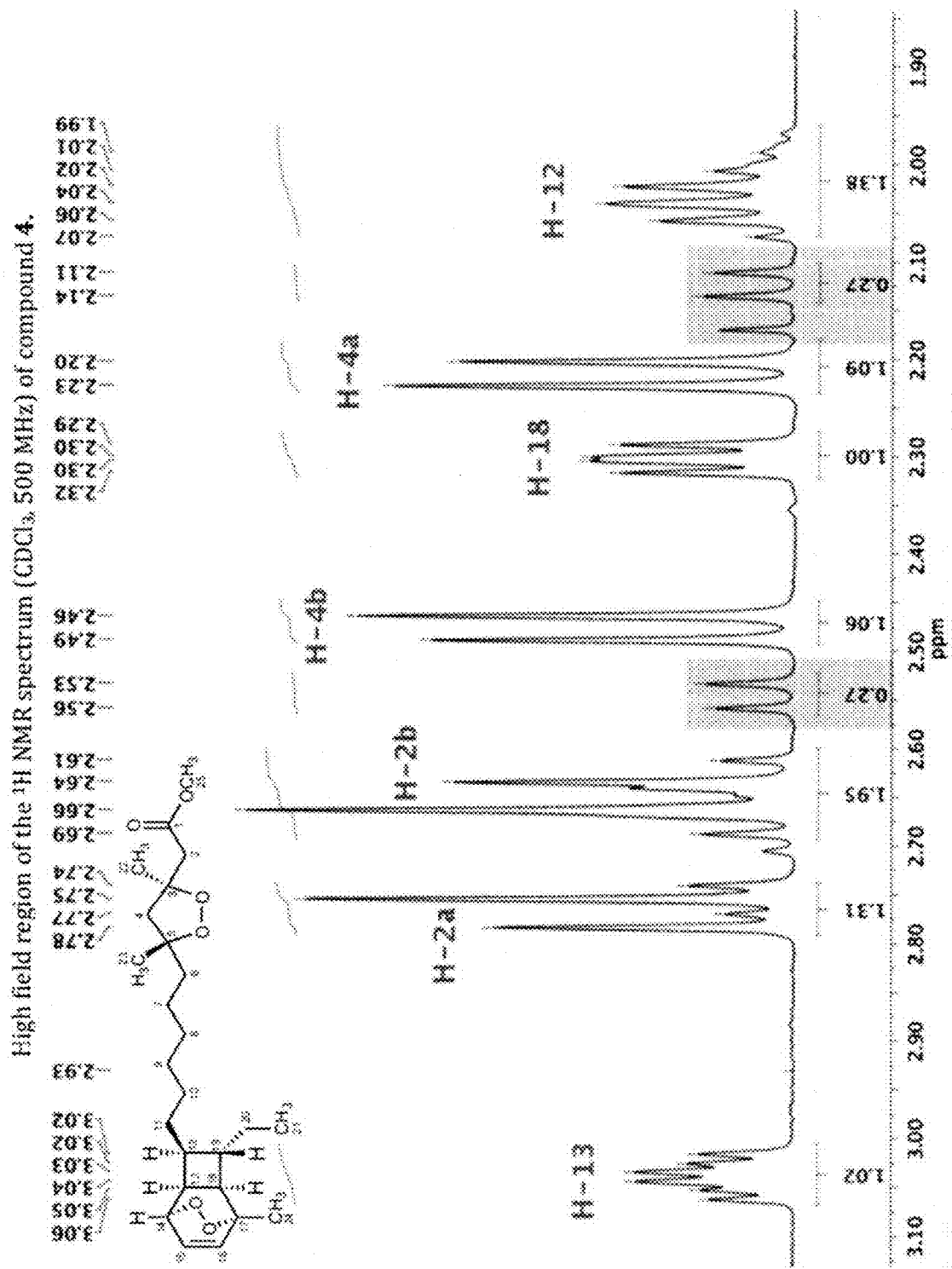
FIG. 16 shows a high field region of the $^1$H NMR spectrum (CDCl$_3$, 500 MHz) of compound (4), according to the present invention.
Figure 17:
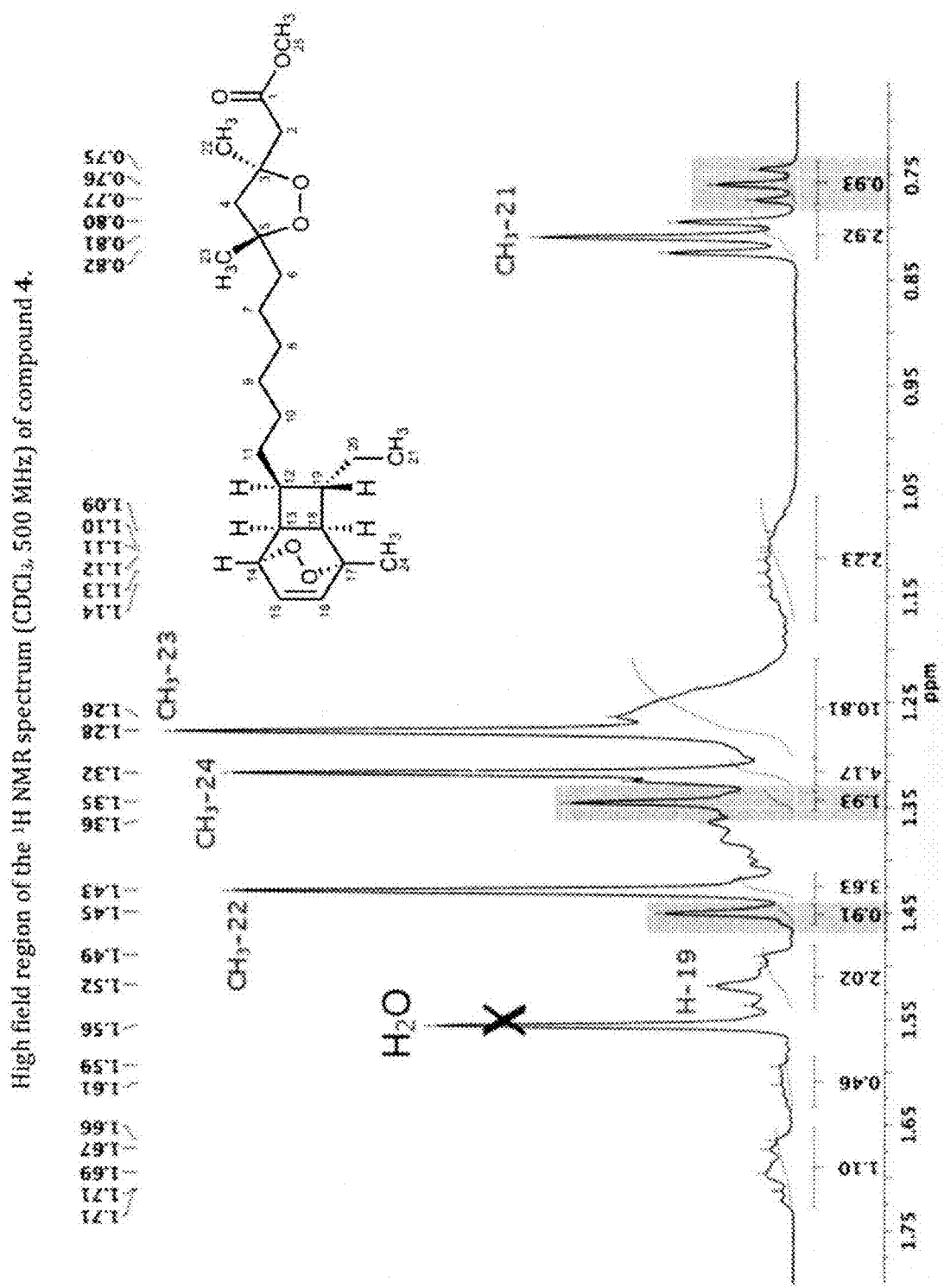
FIG. 17 shows another high field region of the $^1$H NMR spectrum (CDCl$_3$, 500 MHz) of compound (4), according to the present invention.
Figure 18:
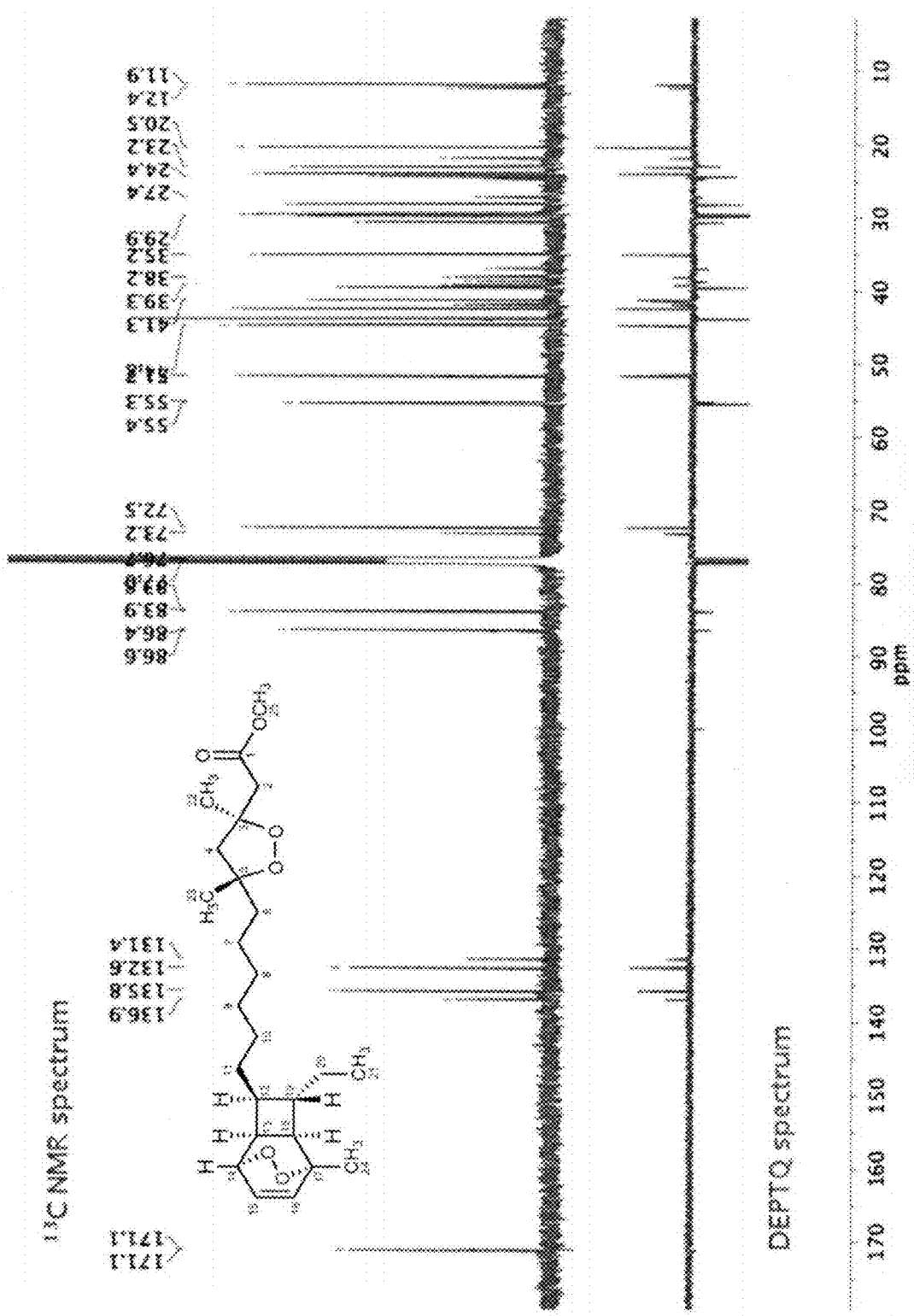
FIG. 18 shows $^{13}$C NMR and DEPTQ spectra (CDCl$_3$, 125 MHz) of plakortinic acid B methyl ester (4), according to the present invention.
Figure 19:
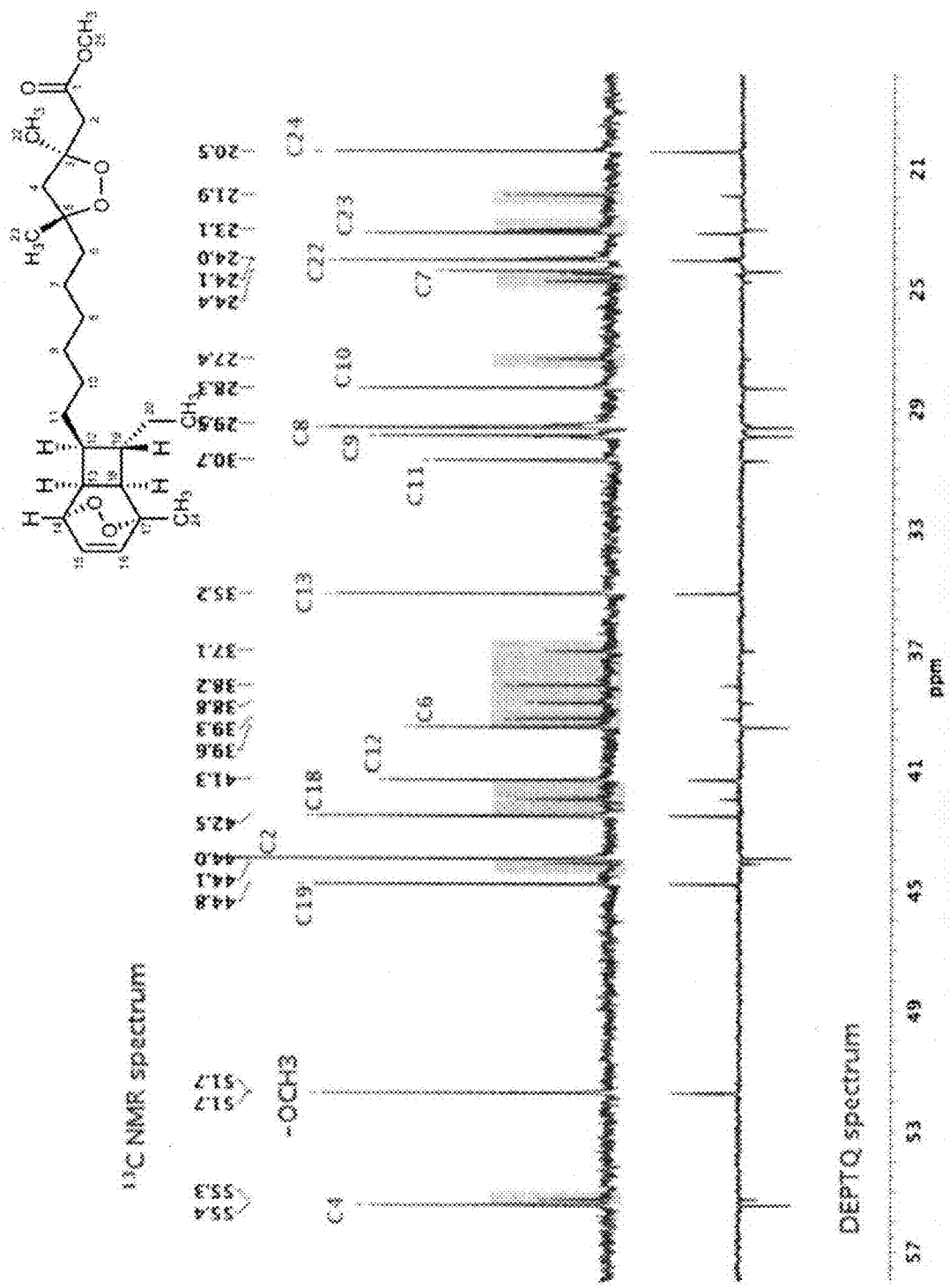
FIG. 19 shows an expanded view of the $^{13}$C NMR and DEPTQ spectra (CDCl$_3$, 125 MHz) of compound (4), wherein the signals highlighted are due to the minor component of the inseparable mixture of diastereomers, according to the present invention.
Figure 20:
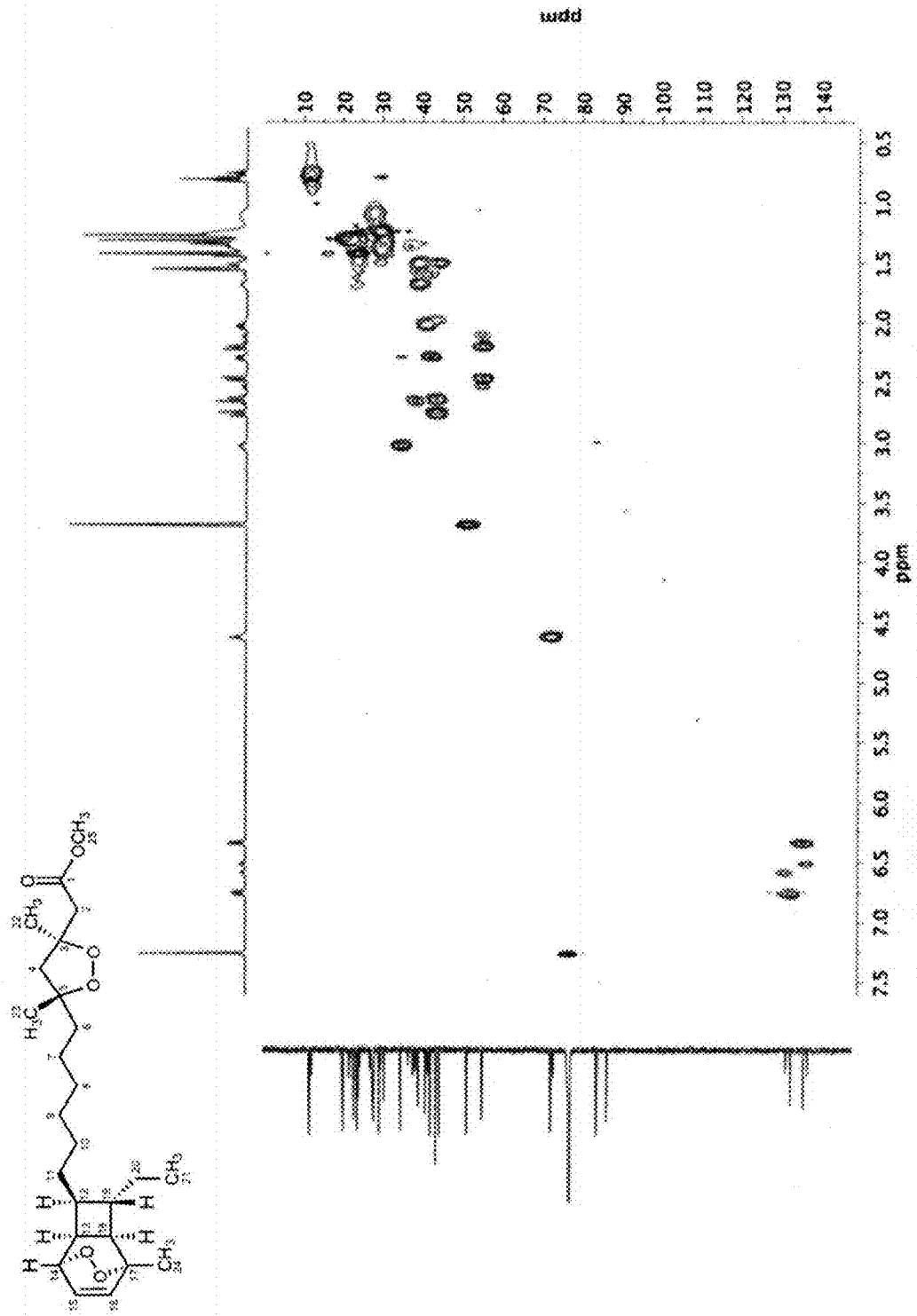
FIG. 20 shows HSQC spectrum (in CDCl$_3$) of plakortinic acid B methyl ester (4), according to the present invention.
Figure 21:
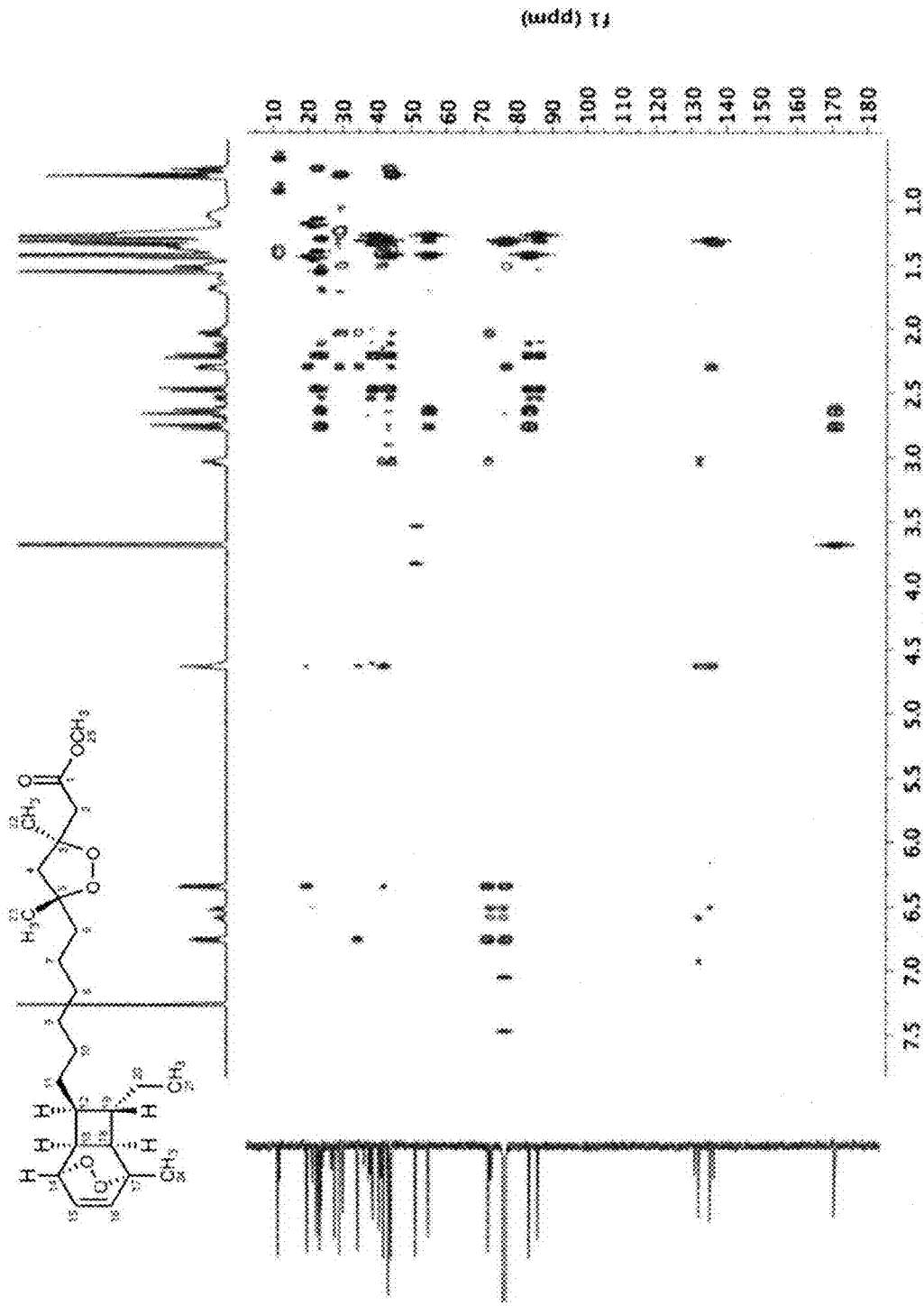
FIG. 21 shows HMBC spectrum (in CDCl$_3$) of plakortinic acid B methyl ester (4), according to the present invention.

Compounds 1 and 2 have common structural features, including almost coincidental molecular formula and specific rotation. Except for a branching methyl group, both have identical 1,2-dioxolane rings and same-length side chains. Considering these structural features, 1 is likely a putative biogenetic precursor of 2 and 3 as shown in FIG. 5.

Compounds 2 and 4 were found to be primarily responsible for the cytotoxicity of the crude extract of the sponge.

Cytotoxicity Assays

Figure 23:
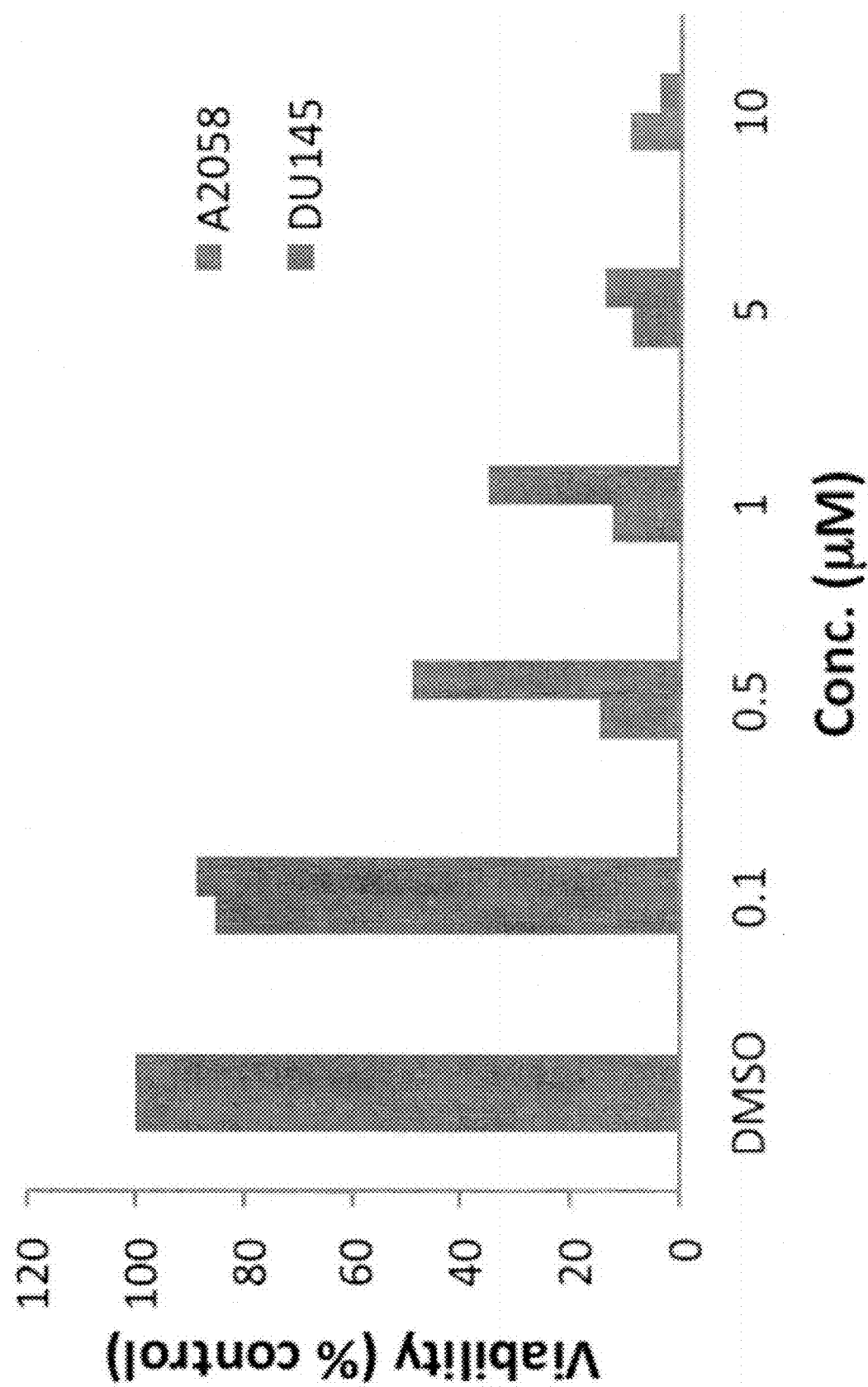
FIG. 23 shows a plot of cytotoxicity of plakortinic acid A (2), according to the present invention.

DU-145 human prostate cancer and A2058 melanoma cell lines were obtained from ATCC. These cells were cultured in RPMI-1640 or DMEM medium containing 10% fetal bovine serum (FBS), 100 units/mL penicillin, and 100 μg/mL streptomycin. All cells were maintained in a 5% CO$_2$ atmosphere at 37° C. To determine the viability of the cells, Promega CellTiter 96 aqueous nonradioactive cell proliferation assays (MTS) were performed as described by the supplier (Promega; Madison, Wis.). Briefly, cells (5000/well) were seeded in 96-well plates and incubated overnight at 37° C. in 5% CO$_2$. Cells were treated for 48 h with each compound. The concentration used was 10 μM. Dimethyl sulfoxide (DMSO) was used as the vehicle control. IC$_{50}$ values of compounds were determined in a dose-dependent manner (0.1, 0.5, 1, 5, 10, 20, and 50 μM). Cell viability was determined by tetrazolium conversion to its formazan dye, and absorbance of formazan was measured at 490 nm using an automated ELISA plate reader. The production of formazan dye was directly proportional to the number of living cells. Each experiment was done in quadruplicate in the absence of a positive control. FIG. 23 shows the behavior of plakortinic acid A (2) in our MTS assay versus A2058 melanoma and DU-145 prostate cancer cells. The cells were significantly more sensitive to compound 2 (IC$_{50}$'s 0.3 and 0.5 μM, respectively) than 4 (IC$_{50}$'s 4.7 and 5.9 μM, respectively).

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

The invention claimed is:

1. An isolated compound consisting of:

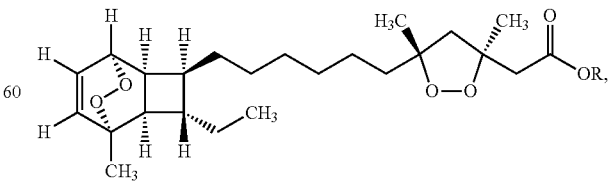

wherein R═CH$_3$.

* * * * *